US009381262B2

(12) United States Patent
Stephens et al.

(10) Patent No.: US 9,381,262 B2
(45) Date of Patent: Jul. 5, 2016

(54) METHODS FOR RADIOLABELING SYNTHETIC POLYMERS

(75) Inventors: Ross Wentworth Stephens, Stirling (AU); Timothy John Senden, Aranda (AU); David Wallace King, Mawson (AU)

(73) Assignee: The Australian National University, Acton, Australian Capital Territory (AU)

( * ) Notice: Subject to any disclaimer, the term of this patent is extended or adjusted under 35 U.S.C. 154(b) by 507 days.

(21) Appl. No.: 12/989,348

(22) PCT Filed: Apr. 23, 2009

(86) PCT No.: PCT/AU2009/000509
§ 371 (c)(1),
(2), (4) Date: Feb. 8, 2011

(87) PCT Pub. No.: WO2009/129578
PCT Pub. Date: Oct. 29, 2009

(65) Prior Publication Data
US 2011/0165070 A1 Jul. 7, 2011

(30) Foreign Application Priority Data
Apr. 24, 2008 (AU) ................................ 2008902064

(51) Int. Cl.
*A61K 51/12* (2006.01)
*A61K 51/08* (2006.01)
*A61K 51/06* (2006.01)
*A61K 41/00* (2006.01)

(52) U.S. Cl.
CPC ......... *A61K 51/1251* (2013.01); *A61K 41/0095* (2013.01); *A61K 51/06* (2013.01); *A61K 51/08* (2013.01); *A61K 51/1272* (2013.01); *A61K 51/1282* (2013.01)

(58) Field of Classification Search
None
See application file for complete search history.

(56) References Cited

U.S. PATENT DOCUMENTS

| 4,247,406 | A | * | 1/1981 | Widder | A61K 9/5094 252/62.54 |
|---|---|---|---|---|---|
| 5,792,241 | A | | 8/1998 | Browitt | |
| 5,855,547 | A | | 1/1999 | Chaney | |
| 6,258,338 | B1 | | 7/2001 | Gray | |
| 6,508,864 | B2 | | 1/2003 | Day | |
| 6,537,518 | B1 | | 3/2003 | Gray | |
| 6,803,069 | B2 | | 10/2004 | Patnaik et al. | |
| 6,977,068 | B1 | | 12/2005 | Nair et al. | |
| 6,998,105 | B2 | | 2/2006 | Ruys et al. | |
| 7,150,867 | B2 | | 12/2006 | Ruys et al. | |
| 2004/0109823 | A1 | * | 6/2004 | Kaplan | 424/1.11 |
| 2004/0220135 | A1 | | 11/2004 | Gray | |
| 2004/0258603 | A1 | | 12/2004 | Yakobson et al. | 423/445 B |
| 2006/0067939 | A1 | | 3/2006 | Buzatu et al. | 424/155.1 |
| 2006/0088519 | A1 | * | 4/2006 | Senga et al. | 424/94.64 |
| 2006/0177373 | A1 | | 8/2006 | Ruys et al. | |
| 2006/0239907 | A1 | * | 10/2006 | Luzzi et al. | 424/1.11 |

FOREIGN PATENT DOCUMENTS

| WO | WO 99/04826 A1 | 2/1999 |
|---|---|---|
| WO | WO 99/04827 A1 | 2/1999 |
| WO | WO 2005/018681 A1 | 3/2005 |
| WO | WO 2006/063418 A2 | 6/2006 |
| WO | WO 2006/116798 A1 | 11/2006 |
| WO | WO 2007/136404 A2 | 11/2007 |
| WO | WO 2008/000045 A1 | 1/2008 |
| WO | 2011/033118 A1 | 3/2011 |

OTHER PUBLICATIONS

Vaisman et al. The role of surfactants in dispersion of carbon nanotubes. 2006 Adv. Colloid Interface Sci. 128-130: 37-46.*
Herba et al., "Hepatic Malignancies: Improved Treatment with Intraarterial Y-90[1]," *Radiology* 169(2):311-314, 1988.
Berge et al., "Pharmaceutical Salts," *Journal of Pharmaceutical Sciences* 66(1):1-19, Jan. 1977.
Ekman et al., "Collection of Aerosols in a Venturi Scrubber," *Industrial and Engineering Chemistry* 43(6):1358-1363, 1951.
Garrean et al., "Complete eradication of hepatic metastasis from colorectal cancer by Yttrium-90 SIRT," *World J. Gastroenterol* 13(21):3016-3019, Jun. 7, 2007.
Gray et al., "Regression of Liver Metastases Following Treatment With Yttrium-90 Microspheres," *Aust. N.Z. J. Surg.* 62:105-110, 1992.
Hede, "Radioactive "Seed" Implants May Rival Surgery for Low-Risk Prostate Cancer Patients," *JNCI* 99:1507-1509, 2007.
Kotzerke et al., "PET aerosol lung scintigraphy using Galligas," *Eur J Nucl Med Mol Imaging* 37:175-177, 2010.
Lerman et al., "Lymphoscintigraphic sentinel node identification in patients with breast cancer: the role of SPECT-CT," *Eur J Nucl Med Mol Imaging* 33:329-337, 2006.
Liu et al., "In vivo biodistribution and highly efficient tumour targeting of carbon nanotubes in mice," *Nature Nanotechnology* 2:47-52, Jan. 2007.
Michalik et al., "Aerosol Preconcentration on a Liquid Electrode," *Talanta* 28:43-47, 1981.

(Continued)

*Primary Examiner* — Michael G Hartley
*Assistant Examiner* — Jennifer Lamberski
(74) *Attorney, Agent, or Firm* — Seed IP Law Group PLLC

(57) ABSTRACT

The present invention relates to a method for preparing a radiolabeled synthetic polymer, the method comprising contacting a synthetic polymer with a carbon encapsulated nanoparticle composite having a radioactive particulate core in an aqueous medium comprising an electrolyte concentration or pH selected to promote short-range attractive forces between the nanoparticles and the synthetic polymer by attenuating long-range electrostatic repulsive forces.

7 Claims, 19 Drawing Sheets

(56) References Cited

OTHER PUBLICATIONS

Nair et al., "*ThromboTrace*, a new diagnostic agent with high specificity to bind fibrin in vivo," *Blood Coagulation and Fibrinolysis* 9(7):716-717, 1998.

Sarin et al., "Accelerated partial breast irradiation using multicatheter brachytherapy," *Nature Clinical Practice Oncology* 4(7):382-383, Jul. 2007.

* cited by examiner

METHODS FOR RADIOLABELING SYNTHETIC POLYMERS

CROSS REFERENCE TO RELATED APPLICATION

This application claims the benefit of Australian Provisional Patent Application No. 2008902064 filed 24 Apr. 2008 which is incorporated herein by reference in its entirety.

FIELD OF THE INVENTION

The present invention relates to methods for the preparation of radiolabelled macromolecular assemblies, such as synthetic polymers (plastics) for use in pharmaceutical and veterinarial preparations. In particular embodiments the invention relates to radiolabelled synthetic polymers for use in diagnostic imaging, regional radiotherapy and targeted radiotherapy.

BACKGROUND OF THE INVENTION

Methods for the production of radiolabelled synthetic polymers are known in the art. Traditional methods include the use of chemical linkers which may attach radionuclides by either salt linkage (i.e. similar to ion exchange resins) or by the use of chelate chemistry. Typically these methods suffer from either low retention of radionuclide or low specific activity due to the limited density of labelling obtainable on the polymer (respectively). More recently chelate derivatives of detergents have been used to radiolabel the surface of carbon nanotubes, but these suffer the same limitation of low rate of labelling as for other chelate derivatives, as well as the low biological tolerance of such detergents [Liu et al, *Nature Nanotechnology* 2:47-52 (2007)]. Another limitation of the use of chelate chemistry is that a given chelating functionality is not suitable for a wide range of different metallic radionuclides. Changing the metal often necessitates changing the chemistry of the chelate. The synthetic radiolabelled polymers may find use in various medical and therapeutic areas. As an example, several types of implants are used in medicine for the treatment of cardiovascular disease and cancer. Thus for example, stents (short cylindrical tubes) are implanted in coronary arteries to increase vessel patency, and the synthetic polymer surface of some stents may include an inhibitor of restenosis to prevent recurrence of an occlusion in the vessel. Endovascular brachytherapy with radioisotopes is one method for preventing reocclusion during the short post-operative period, in which the stent includes a radioisotope to inhibit proliferation of smooth muscle cells. In the treatment of cancer, radiolabelled synthetic polymers may be used in several forms e.g. microspheres, that can be locally instilled in the afferent blood supply to a selected organ, for the purpose of regional delivery of a therapeutic dose of a radioisotope that can ablate a tumour. High levels of specific activity of labelling on the polymer and strong retention of the radionuclide on the polymer are desirable in such a therapeutic strategy, in order that a large dose of activity is delivered in a small amount of material and the effect of the radiation can be reliably restricted to the target tissue. Methods known in the art for radiolabelling synthetic polymers are limited by 1) the degree to which the synthetic polymer may be labelled and or 2) the avidity of the labelling, and 3) in their application to a wide range of different metallic radionuclides.

There is a need for improved methods of preparing radiolabelled synthetic polymers that overcome or avoid one or more disadvantages or limitations of the known methods.

SUMMARY OF THE INVENTION

The present invention aims to provide an improved method for the preparation of radiolabelled synthetic polymers (plastics) or provide an alternative to the prior art.

In accordance with a first aspect of the invention, there is provided a method for preparing a radiolabelled synthetic polymer, the method comprising contacting a synthetic polymer with a carbon encapsulated nanoparticle composite having a radioactive particulate core in an aqueous medium comprising an electrolyte concentration or pH selected to promote short-range attractive forces between the nanoparticles and the synthetic polymer by attenuating repulsive electrostatic forces.

In one embodiment the carbon encapsulated nanoparticle composite is FibrinLite.

In one embodiment the carbon encapsulated nanoparticle composite comprises an anionic surfactant. In one embodiment the anionic surfactant is sodium deoxycholate.

In one embodiment the electrolyte concentration and the pH are selected to promote short range attractive forces.

In one embodiment the aqueous medium comprises an anionic surfactant. In one embodiment the anionic surfactant is sodium deoxycholate.

In one embodiment the electrolyte is a simple electrolyte. In one embodiment the simple electrolyte is selected from the group consisting of Na, K, and Ca.

In one embodiment the simple electrolyte concentration of the aqueous medium is in the range of greater than about 1 millimolar to about 150 millimolar. In one embodiment the pH of the aqueous medium is about 3.5. In one embodiment the aqueous medium comprises an electrolyte concentration corresponding to about 15 millimolar NaCl and has a pH about 3.5. In one embodiment the aqueous medium comprises an electrolyte concentration corresponding to about 80 millimolar NaCl and has a pH about neutral.

In one embodiment the electrolyte is a polycation. In one embodiment the polycation is selected from the group consisting of polylysine, protamine and aprotinin.

In one embodiment the aqueous medium comprises a polycation concentration in the range of greater than about 5 nanomolar to about 4000 nanomolar. In one embodiment the aqueous medium comprises a polycation concentration corresponding to about 30 nanomolar polylysine. In one embodiment the aqueous medium comprises a polycation concentration corresponding to about 2500 nanomolar protamine.

In one embodiment the radioactive particulate core comprises a radioactive isotope or radionuclide selected from the group consisting of $^{99m}$Tc, $^{198}$Au, $^{64}$Cu, $^{51}$Cr, $^{67}$Ga, $^{68}$Ga, $^{166}$Ho, $^{111}$In, $^{177}$Lu, $^{103}$Pd, $^{82}$Rb, $^{186}$Re, $^{153}$Sm, $^{89}$Sr, $^{90}$Y, $^{89}$Zr, and $^{192}$Ir.

In one embodiment the radioactive particulate core comprises $^{99m}$Tc.

In one embodiment the synthetic polymer is selected from the group consisting of polystyrene, polytetrafluorethylene (PTFE), polyethylene terephthalate, and polylactide (PLA).

In one embodiment the synthetic polymer comprises a suspension or dispersion of polymers.

In one embodiment the synthetic polymer is in the form of or comprises a macromolecular assembly. In one embodiment the macromolecular assembly comprises a polymer bead.

In one embodiment the synthetic polymer is comprised in or on a catheter, a fibre, a rod or filament, a membrane, a wafer, a mesh or gauze, a porous sponge, a tube or stent, a bead or capsule or microparticles in the form of microspheres of known dimensions, a nanoparticle, a liposome.

In one embodiment the synthetic polymer comprises microparticles of a size range that enables entrapment in the small blood vessel network of a tissue, e.g. at the site of a tumour.

In one embodiment the method further comprises separating radiolabelled synthetic polymer from unlabelled synthetic polymer and or from free nanoparticle composite.

In a second aspect of the invention, there is provided a radiolabelled entity comprising a synthetic polymer complexed with a carbon encapsulated nanoparticle composite having a radioactive particulate core.

In one embodiment the radiolabelled entity is a medical device.

In one embodiment the radiolabelled entity comprises a plurality of distinct radiolabels.

In one embodiment the radiolabelled entity comprises a radiolabel suitable for imaging and a radiolabel suitable for therapeutic application.

In a third aspect of the invention there is provided a method of preparing a radiolabelled medical device, the method comprising contacting a radiolabelled synthetic polymer comprising a carbon encapsulated nanoparticle composite having a radioactive particulate core with a medical device under conditions suitable for the incorporation of said radiolabelled synthetic polymer into or onto said medical device.

In one embodiment the medical device of the second or third aspect is selected from a diagnostic device and a therapeutic device.

In one embodiment of the second or third aspect the medical device comprises a radiolabelled synthetic polymer comprised in or on a catheter, a fibre, a rod or filament, a membrane, a wafer, a mesh or gauze, a porous sponge, a tube or stent, a bead or capsule or microparticles in the form of microspheres of known dimensions, a nanoparticle, a liposome.

In one embodiment the device of the second or third aspect is an implantable medical device.

In one embodiment the device of the second or third aspect is a stent.

In one embodiment the device of the second or third aspect is a synthetic polymer microparticle suitable for instillation in the local arterial blood supply of a selected target organ as a selective internal radiation therapy, comprising a particle size so as to lodge in the arterial blood capillary network of said target organ.

In one embodiment the medical device of the second or third aspect is a veterinary device.

In a fourth aspect the invention provides a method of radiation therapy of a patient, the method comprising administering to said patient a therapeutically effective amount of a radiolabelled synthetic polymer, wherein said radiolabelled synthetic polymer comprises a synthetic polymer in association with a carbon encapsulated nanoparticle composite having a radioactive particulate core.

In one embodiment the radiolabelled synthetic polymer is in the form of, or incorporated into or onto, a bead, microparticle or microsphere.

In one embodiment the method of radiation therapy of a patient is selective internal radiation therapy.

In one embodiment the therapy is treatment of cancer.

In one embodiment the cancer is metastatic (secondary) cancer present in the liver, originating from primary tumours of the colon, rectum, or breast. In one embodiment the cancer is primary liver cancer (hepatocellular carcinoma).

In a fifth aspect of the invention, there is provided a method for preparing a synthetic polymer complexed with an inactive progenitor of a radioisotope, the method comprising contacting a synthetic polymer with a carbon encapsulated nanoparticle composite having a particulate core comprising an inactive progenitor of a radioisotope in an aqueous dispersion comprising an electrolyte concentration or pH selected to promote short-range attractive forces between the nanoparticles and the synthetic polymer by attenuating long-range electrostatic repulsive forces.

In a sixth aspect of the invention there is provided a complex comprising a synthetic polymer and a carbon encapsulated nanoparticle composite having a particulate core comprising an inactive progenitor of a radioactive isotope.

In a seventh aspect of the invention there is provided a method for radiolabelling a synthetic polymer, the method comprising the steps of (a) contacting a synthetic polymer with a carbon encapsulated nanoparticle composite having a particulate core comprising an inactive progenitor of a radioisotope in an aqueous dispersion comprising an electrolyte concentration or pH selected to promote short-range attractive forces between the nanoparticles and the synthetic polymer by attenuating long-range electrostatic repulsive forces; and (b) activating said inactive progenitor to generate a radioactive isotope.

In one embodiment of the fifth, sixth or seventh aspect the inactive progenitor of a radioisotope is stable isotope of boron (boron-10).

In one embodiment of the fifth, sixth or seventh aspect the synthetic polymer comprises a suspension or dispersion of polymers.

In one embodiment of the fifth, sixth or seventh aspect the synthetic polymer is comprised in or on a catheter, a fibre, a rod or filament, a membrane, a wafer, a mesh or gauze, a porous sponge, a tube or stent, a bead or capsule or microparticles in the form of microbeads of known dimensions, a nanoparticle, a liposome.

In one embodiment of the fifth, sixth or seventh aspect the method further comprises incorporating said synthetic polymer into or onto a medical device. In one embodiment the synthetic polymer is incorporated into or onto a medical device prior to activating. In one embodiment the method further comprises administering said medical device to a subject prior to said activating. In one embodiment said administering comprises implanting said medical device in a subject prior to said activating.

In one embodiment the activating comprises exposing said progenitor to a neutron beam.

In an eighth aspect the invention provides a method of radiation therapy of a patient, the method comprising administering to said patient an amount of a complex comprising a synthetic polymer and a carbon encapsulated nanoparticle composite having a particulate core comprising an inactive progenitor of a radioactive isotope, wherein said amount is a therapeutically effective amount when said inactive progenitor is activated, and activating said inactive progenitor to generate a radioactive isotope.

In one embodiment said inactive progenitor of a radioactive isotope is boron (boron-10).

In one embodiment said activating comprises exposing said progenitor to a neutron beam.

In a ninth aspect the invention provides a method of imaging a medical procedure in a patient, the method comprising administering to said patient a complex comprising a synthetic polymer and carbon encapsulated nanoparticle composite having a radioactive particulate core, and detecting said complex in said subject.

In one embodiment the medical procedure comprises regional therapy of a disease.

In one embodiment the detecting comprises gamma camera imaging of said radioactivity.

In one embodiment the synthetic polymer comprises microparticles or nanoparticles.

In one embodiment said method comprises administering to said patient a radioisotope suitable for therapy of a disease, a radioisotope suitable for imaging or a combination thereof.

In one embodiment the complex comprises dual labelled synthetic polymer. In one embodiment the dual labelled synthetic polymer comprises a radioactive isotope suitable for therapy and a radioactive isotope suitable for imaging.

The summary of the invention described above is not limiting and other features and advantages of the invention will be apparent from the following detailed description of the preferred embodiments, as well as from the claims.

BRIEF DESCRIPTION OF THE DRAWINGS

Preferred forms of the present invention will now be described with reference to the accompanying drawings in which.

ABBREVIATIONS

Figure 1A:
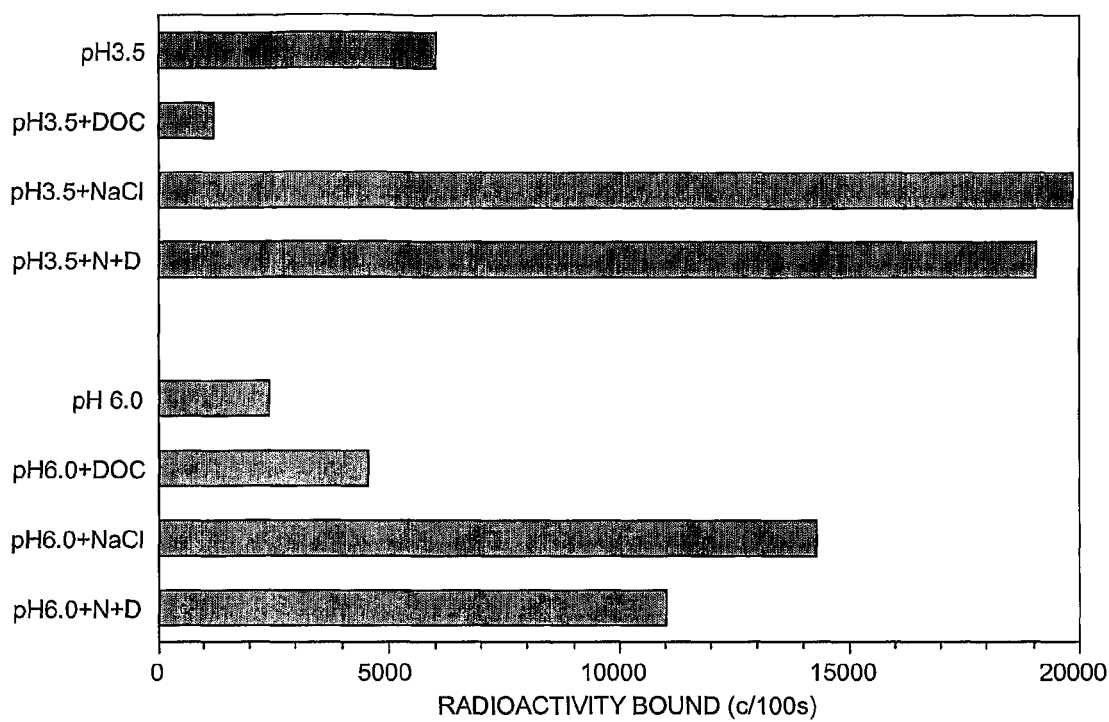
FIG. 1a: Binding of Tc-99m FibrinLite particles to polystyrene wells under various buffer conditions: 500 µM sodium citrate pH 3.5 ("pH 3.5"); 500 µM sodium citrate pH 3.5 plus 10 µM sodium deoxycholate ("pH 3.5 DOC"); 500 µM sodium citrate pH 3.5 plus 150 mM NaCl ("pH 3.5+NaCl"); 500 µM sodium citrate pH 3.5 plus 10 µM DOC plus 150 mM NaCl ("pH 3.5+N+D"); the annotations "pH 6.0", "pH 6.0+DOC", "pH 6.0+NaCl", and "pH 6.0+N+D" have corresponding meanings but at pH 6.0 rather than pH 3.5. The bars represent means of duplicate wells.

For convenience, the following abbreviations used in this specification are listed below.

As used herein the term "SPECT" is an abbreviation for single photon emission computed tomography.

As used herein the term "PET" is an abbreviation for positron emission tomography.

As used herein the term "SIRT" is an abbreviation for selective internal radiation therapy.

As used herein the term "SMPS" is an abbreviation for scanning mobility particle sizing.

As used herein the term "MCE" is an abbreviation for mixed cellulose ester.

As used herein the term "PTFE" is an abbreviation for polytetrafluorethylene.

As used herein the term "ePTFE" is an abbreviation for expanded polytetrafluorethylene.

As used herein the term "PBT" is an abbreviation for poly(butylene terephthalate).

As used herein the term "PEO" is an abbreviation for poly(ethylene oxide).

As used herein the term "PLA" is an abbreviation for polylactide.

As used herein the term "PGA" is an abbreviation for polyglycolide.

As used herein the term "DOC" is an abbreviation for sodium deoxycholate.

It will be understood that the description herein regarding the preparation of, and use of, carbon encapsulated nanoparticle composites having a radioactive particulate core (such as FibrinLite nanoparticles) in the preparation of radiolabelled synthetic polymers applies mutatis mutandis to the use of carbon encapsulated nanoparticle composites having a particulate core comprising an inactive progenitor of a radioisotope, as appropriate, as will be recognised by the skilled addressee (such as the use of inactive progenitors rather than active radioisotopes and the activation step in the case of the inactive precursor embodiments).

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age, weight and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

In the context of this specification, the term "comprising" means "including principally, but not necessarily solely". Furthermore, variations of the word "comprising", such as "comprise" and "comprises", have correspondingly varied meanings. Hence, the term "comprising" and variations thereof is used in an inclusive rather than exclusive meaning such that additional integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc, and inclusive of any value and range between the integers which is reasonable in the context of the range stated, such as 5.5, 6.5, 7.5, 5.5 to 8.5 and 6.5 to 9, etc.

In the context of this specification, the term "plurality" means any number greater than one.

To the extent that it is permitted, all references cited herein are incorporated by reference in their entirety.

DESCRIPTION OF PREFERRED AND OTHER EMBODIMENTS

The present invention will now be described in more detail, including, by way of illustration only, with respect to the examples which follow.

The inventors have discovered that suitable conditions of pH and or electrolyte concentration can be selected that facilitate the reduction of repulsive charges between nanoparticle composites of carbon-encapsulated radionuclides and synthetic polymers and thus enable short-range attractive forces to dominate over long-range electrostatic repulsive forces, such that the nanoparticle composites (such as FibrinLite nanoparticles) become virtually irreversibly bound to a polymer surface. The present invention thus relates to a method for the use of nanoparticle composites of carbon-encapsulated radionuclides (such as FibrinLite) for high specific activity radiolabelling of synthetic polymers capable of attractive hydrophobic dispersion interactions or ion correlation with the graphite that comprises the external surface of the nanoparticles.

In specific embodiments, the methodology permits high avidity radiolabelling of synthetic polymers, for example those used in research applications and those used in medical applications for diagnosis or therapy, such as medical devices including therapeutic implants for treatment of cardiovascular disease and cancers. In preferred embodiments the high avidity radiolabelling of the synthetic polymer is substantially irreversible under conditions typically encountered by the labelled synthetic polymers and medical devices. In specific embodiments the high avidity labelling of the synthetic polymer is such that there is less than about 10% dissociation under in vivo conditions.

U.S. Pat. No. 6,977,068 entitled "Method for detection of fibrin clots" dated 20 Dec. 2005 to Nair et al. describes methods for the use of carbon-encapsulated radionuclide nanoparticles in the detection of fibrin clots. International Patent Application No. PCT/AU2006/000554 filed 28 Apr. 2006 and published as WO 2006/116798 A1, entitled "A method of forming an injectable radioactive composition of a carbon encapsulated radioactive particulate" describes a process for the production of an injectable formulation of carbon encapsulated nanoparticles. The process described therein can be referred to as "FibrinLite process" and the nanoparticles so-produced may be referred to as "FibrinLite". To the extent permitted, the entire contents of both U.S. Pat. No. 6,977,068 and PCT/AU2006/000554 (WO 2006/116798) are incorporated herein by reference. As described herein the present inventors have discovered a method for using the carbon encapsulated nanoparticles (such as FibrinLite nanoparticles) that can provide high specific activity and high avidity radiolabelling of synthetic polymers.

By providing a method by which radiolabelled synthetic polymers may be prepared using FibrinLite nanoparticles, the present inventors take advantage of the carbon encapsulation process (see PCT/AU2006/000554) which wraps the metallic isotope in a carbon cage, so that it becomes physically isolated from contact with its external environment, an especially valuable property for the particles and hence the synthetic polymers, particularly when they are to be used in vivo. The potential for leaching and bio-uptake of the radioactive metal ions in vivo of the radiolabelled synthetic polymer is virtually non-existent because only the carbon exterior of the nanoparticle composite is exposed to the biological environment in vivo.

Synthetic Polymers and Medical Applications

The method of the present invention may find use, for example, in the preparation of devices useful in medicine for therapeutic or diagnostic application. In this context any medical device, including for example carriers and implants, which, when bound to or with a radioactive isotope, will provide a therapeutic or diagnostic benefit may be used in the invention.

As one example, the medical device may be an implantable device used in medicine for the treatment of vascular disease, for example cardiovascular disease, such as a vascular graft, endoprosthesis or stent. Other medical devices may also be used, such as catheters which are minimally invasive. The vascular graft may be of any suitable shape or design and may, for example, include a hollow tubular body having an inner and an outer hydrophobic surface. The medical device may be a small calibre vascular graft, such as an expanded polytetrafluoroethylane (ePTFE) vascular graft. For purposes of this invention, the term "vascular graft" includes endoprostheses which are generally introduced via catheter or during a surgical procedure. Thus stents (typically in the form of short cylindrical tubes) are implanted in coronary arteries to increase vessel patency, and the synthetic polymer surface of some stents may include an inhibitor of restenosis to prevent recurrence of an occlusion in the vessel. Endovascular brachytherapy with radioisotopes is one method for preventing reocclusion during the short post-operative period, in which the stent includes a radioisotope to inhibit proliferation of smooth muscle cells. Other types of implants include macrobeads, "seeds", wires, fibres or filaments, gauze or mesh such as for local irradiation of an organ bearing a tumour, such as in brachytherapy of breast or prostate cancer.

Methods for the treatment of cancer by local administration of radioactive materials are known and include, for example, where the radioactive material is incorporated into small particles, seeds, wires and similar configurations that can be directly implanted into the cancer. These forms are all contemplated within the scope of embodiments of the invention. This form of brachytherapy is typically used for local irradiation of a tumour in e.g. a breast or the prostate, where "seeds" bearing a therapeutic isotope are implanted in the organ. [Hede, *J Natl Cancer Inst* 99:1507-1509 (2007); Sarin et al, *Nature Clin Pract Oncol* 4:382-383 (2007)].

In another form of cancer treatment, synthetic polymers may be used in several forms, such as microbeads, microparticles and microspheres, that can be locally instilled from a catheter into the afferent (arterial) blood supply to a selected organ (for example a diseased organ), for the purpose of regional delivery of a therapeutic dose of a radioisotope that can ablate a tumour in that organ. These forms are all contemplated within the scope of embodiments of the invention. In this form of regional radiotherapy, the diameter of the beads is chosen so that the beads will lodge in the arterial blood capillary network of the tumour. In such applications the radioisotope is typically selected from those that have short-range, high-energy emissions capable of killing proliferating cells, such as $^{32}$P, $^{153}$Sm, $^{90}$Y, $^{125}$I, $^{192}$Ir, $^{103}$Pd, $^{111}$In, $^{166}$Ho.

In one example of such a technique, the radioactive particles are administered into the blood supply of a target organ, such as the liver, in order to ablate secondary (metastatic) tumours originating from a primary tumour in the colon or rectum. This is generally known in the art as selective internal radiation therapy (SIRT) [Garrean et al, *World J Gastroenterol* 13:3016-3019 (2007)]. Examples of methods and devices suitable for use in such methods are included in the following US patents and patent applications, the entire contents of each of which is herein incorporated by reference, U.S. Pat. No. 5,855,547 dated 23 Mar. 2000 to Gray entitled "Particulate material"; U.S. Pat. No. 7,150,867 dated 19 Dec. 2006 to Ruys et al entitled "Radioactive-coated particulate material"; U.S. Pat. No. 6,258,338 dated 10 Jul. 2001 to Gray entitled "Hollow or cup-shaped microparticles and methods of use"; U.S. Pat. No. 6,537,518 dated 25 Mar. 2003 to Gray entitled "Particulate material"; U.S. Pat. No. 6,998,105 dated 14 Feb. 2006 to Ruys and Gray entitled "Low density radionuclide-containing particulate material"; United States Patent Publication No. US 2004/0220135 published 4 Nov. 2007 entitled "Combination therapy for treatment of neoplasia" and United States Patent Publication No. US 2006/0177373 published 10 Aug. 2006 entitled "Low density radionuclide-containing particulate material". Examples of commercially available material for selective internal radiation therapy include Sir-Spheres microspheres typically loaded with yttrium-90, (Sirtex Medical Limited Australia) and TheraSpheres, which consist of glass microspheres containing yttrium-90, produced by MDS Nordion and approved by FDA in the US for treatment of primary liver cancer (hepatocellular carcinoma).

Another method of use is in the form of radiolabelled nanoparticles for intra-operative imaging such as for the purpose of identification and localization of lymph nodes draining a tumour site, e.g. imaging of sentinel nodes in breast cancer patients. In this technique radiolabelled nanoparticles are injected directly into a tumour site, from where they migrate in the interstitial fluid and enter the lymph draining a tumour site, ultimately to accumulate in the nearest (sentinel) lymph node. The isotope in this case would be selected from those most suitable for imaging, such as $^{99}$Tc. [Lerman et al, *Eur J Nucl Med Mol Imaging* 33:329-337 (2006)]. In this application the particles are small enough that they will diffuse in the interstitial fluid in a tissue and be collected in the lymph drainage; accordingly nanoparticles rather than microparticles are typically used.

Another method of use is in boron neutron capture therapy (BNCT). This method involves the accumulation of a stable isotope precursor (or progenitor), such as boron-10, at the site of disease, typically a tumour site such as glioblastoma, and the application of a beam of low energy neutrons to the accumulated isotope. Boron-10 in or adjacent to the tumor cells disintegrates after capturing a neutron and the high energy heavy charged particles produced destroy only the cells in close proximity to it, primarily cancer cells, leaving adjacent normal cells largely unaffected. The present invention provides that a synthetic polymer, in free form such as in solution or dispersion, or comprised in or on a medical device, may be prepared with a high avidity and or high density of radioactive precursor, such as a stable isotope of boron to permit improved delivery and concentration of the isotope at the treatment site.

It is to be noted that reference herein to use in medicine will be understood to be equally applicable to human and non-human, such as veterinary, applications. Hence it will be understood that, except where otherwise indicated, reference to a patient, subject or individual means a human or non-human, such as an individual of any species of social, economic or research importance including but not limited to members of the genus ovine, bovine, equine, porcine, feline, canine, primates, rodents and lagomorphs.

Similarly, it is to be noted that reference herein to "medical" device will be understood to be equally applicable to medical devices suitable for use in human applications and to medical devices suitable for use in non-human, such as veterinary, applications.

As used herein the term "device" will be understood to include devices which may be used in therapy, including preventative therapy and treatment of an actual condition or symptom, and devices which may be used in diagnosis, including where the diagnosis is performed on or in the body of a patient and where the diagnosis is performed on or with a sample obtained from the body of a patient. Accordingly, the term "device" as used herein includes therapeutic devices and diagnostic devices.

As used herein "diagnosis" will be understood to include investigative procedures performed in circumstances where a disease or condition is suspected, such as for initial investigation, prognosis, progression of a disease or condition whether in the presence or the absence of therapy, and in circumstances where no such suspicion exists but where investigation is desired, such as for the purposes of health checks, population screening or research.

Radioactive Isotopes and Inactive Precursors

The skilled addressee will appreciate that, because the method of the present invention permits the FibrinLite particles to be used in labelling a synthetic polymer, any radioisotope that may be incorporated in the FibrinLite nanoparticle may therefore be used as the radioisotope by which a synthetic polymer is radiolabelled. Similarly, any inactive progenitor of a radioisotope that may be incorporated in the FibrinLite nanoparticle and that is capable of activation to generate a radioisotope may be used in the preparation of an inactive precursor-labelled synthetic polymer and hence in preparation of a radiolabelled synthetic polymer.

As described in PCT/AU2006/000554 a diverse range of radioisotopes may be incorporated in FibrinLite nanoparticles, including those that emit gamma radiation, such as Tc-99m, Ga-67; those that emit beta radiation, such as yttrium-90; those that emit alpha radiation, such as Bi-213; and those that emit positron radiation, such as Cu-64. Any suitable metallic radioactive isotope may be utilised, including $^{198}$Au, $^{64}$Cu, $^{213}$Bi, $^{57}$Co, $^{51}$Cr, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, $^{169}$Yb, $^{66}$Ga, $^{99m}$Tc, $^{94m}$Tc, $^{89}$Zr, $^{86}$Y, $^{192}$Ir. Similarly any suitable inactive precursor of a radioisotope may be utilised in relevant embodiments, including $^{10}$B.

The range of isotopes that may be used in the FibrinLite nanoparticles and hence in the methods of the present invention, include those that are ideally suited for diagnostic imaging applications, such as single photon computed tomography (SPECT) using Tc-99m or Ga-67, and positron emission tomography (PET) using Cu-64 or Zr-89. Additionally, included also are isotopes suitable for targeted radiotherapy as described above, such as those already in use for ablation of certain types of tumours, for example Y-90 coated SIR-Spheres microspheres that are used for selective internal radiation therapy (SIRT) of liver metastases of colorectal cancer [Gray et al, *Aust NZ J Surg* 62:105-110 (1992)]. The present invention provides alternative methods by which such labelled entities and others may be prepared, as suitable for diagnostic imaging of tumours or as suitable for tumour therapy.

Typically the radioisotopes most suitable for imaging may not be the most suitable for therapy. The present invention also includes the possibility of dual labelling of synthetic polymers such as microspheres, in which one isotope is selected for optimal imaging, and the other isotope for optimal therapy. This composite is intended to allow more reliable dosimetry in the use of the microspheres for tumour therapy, using the imaging to facilitate localisation of the therapeutic dose and also to enable external estimation of the dose of therapeutic isotope that has been delivered to a given organ site, and the dose delivered to a tumour versus the normal host tissue. A dual labelled device may be prepared by any suitable method, such as by contacting a device with two distinctly labelled synthetic polymers or contacting a device with a synthetic polymer labelled with two distinct radiolabels; in which case for the latter the dual labelled synthetic polymer may be prepared using two differently labelled FibrinLite compositions (simultaneously or sequentially) or by preparing a single FibrinLite composite which itself is dual-labelled. Typically two separate preparations of FibrinLite are prepared, using two different isotopes, and a mixture of the two preparations is used to radiolabel the synthetic polymer. By changing the ratio of the two preparations in the mixture, adjustment can be made of the therapeutic activity while maintaining a suitable level of activity for imaging.

For some applications, typically for some therapeutic applications, it may be advantageous to generate a radioactive isotope locally in a target organ site after injection of particles containing the inactive progenitor, such as by exposure of the organ site to a neutron beam. In this embodiment the nanoparticles may comprise an encapsulated stable metallic isotope, e.g. boron-10 ($^{10}$B), that is the inactive progenitor of a radioactive isotope, that may be activated by exposure to a suitable activator, such as a neutron beam to form a therapeutic isotope in situ. By this means very short-lived, high-energy isotopes, e.g. alpha-emitters, may be more safely and efficaciously generated locally for the purpose of tumour ablation.

Formulation of Nanoparticle Composites

The carbon encapsulated nanoparticle composite having a radioactive particulate core (referred to herein as "FibrinLite", e.g., an aqueous dispersion of carbon encapsulated $^{99m}$Tc, $^{113m}$In, $^{111}$In, $^{198}$Au, $^{64}$Cu, $^{213}$Bi, $^{57}$Co, $^{51}$Cr, $^{165}$Dy, $^{169}$Er, $^{59}$Fe, $^{153}$Gd, $^{166}$Ho, $^{177}$Lu, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, or $^{169}$Yb nanoparticles having a diameter of 10 to 500 nanometers) may be prepared according to PCT/AU2006/000554 entitled "A method of forming an injectable radioactive composition of a carbon encapsulated radioactive particulate" (published as WO 2006/116798), the entire contents of which are herein incorporated by reference. Thus the composite may typically be prepared as a neutral or slightly acid pH, stable aqueous dispersion of nanoparticles comprising carbon-encapsulated radionuclide.

It will be understood that a person skilled in the art will be aware that methods of producing an aqueous dispersion of carbon encapsulated nanoparticle composites may include a step of aqueous capture of a radioactive aerosol and that this step may be achieved in a number of ways. For example, the step of aqueous capture of a radioactive aerosol used to make carbon encapsulated nanoparticle composites may include but not be limited to the following:

1. Collection of the aerosol in a Venturi scrubber, for example according to the method of Ekman and Johnstone, published in Industrial and Engineering Chemistry (1951) volume 43, part 6, pages 1358 to 1363.
2. Concentration of the aerosol on a liquid electrode, for example according to the method of Michalik and Stephens, published in Talanta (1981) volume 28, part 1, pages 43 to 47.
3. Use of a cyclone device, for example the cyclone device disclosed by P. J. Day in U.S. Pat. No. 6,508,864 (published on Jan. 21, 2003).

In one exemplary embodiment the carbon encapsulated nanoparticle composites may be prepared using the process described in PCT/AU2006/00054, wherein the process involves capture of the radioactive aerosol in water utilising a Browitt precipitator described in U.S. Pat. No. 5,792,241 the entire contents of which are herein incorporated by reference.

The dispersion of nanoparticles may contain a very low (for example, in the range of about 1 micromolar to about 20 micromolar, typically about 10 micromolar) concentration of an anionic surfactant, such as sodium deoxycholate, which is compatible with and may be injected into, the blood circulation of a living subject. Typically, in therapeutic or in vitro diagnostic applications of the radiolabelled entity, any anionic surfactant approved by regulatory authorities for intravenous use (e.g., injection) in humans or animals as the case may be used.

As described in PCT/AU2006/000554 an exemplary radionuclide is Tc-99m. The nanoparticles can each carry tens of thousands or more of isotope atoms in their core, so that very high levels of specific activity can readily be obtained that are well above those obtainable with traditional labelling methods. For FibrinLite, and using Tc-99m as the model encapsulated radioisotope, a Tc-99m loading in the range of from about 1 to about 100 mCi, about 5 to about 100 mCi, about 7.5 to about 95 mCi, about 10 to about 90 mCi, about 15 to about 85 mCi, about 20 to about 80 mCi, about 25 to about 75 mCi, about 30 to about 70 mCi, about 35 to about 65 mCi, about 40 to about 60 mCi, about 45 to about 55 mCi, or about 50 to about 55 mCi may be prepared. A typical preparation of particles can readily be made so as to contain between about 1 and about 30 mCi in 2 mL of aqueous suspension, as desired. From vapour phase characterization of the particles using scanning mobility particle sizing (SMPS), it can be shown that the suspension can contain approximately 50 µg of nanoparticle material, so that the specific activity can be made as high as 600 mCi/mg, or over 22 GBq/mg. The specific activity of the preparation may be adjusted as desired by varying the activity of isotope used to load the crucible in the aerosol generator.

As described in PCT/AU2006/000554 a broad range of suitable radioactive isotopes may be used in the FibrinLite process and thus it will be appreciated that a broad range of isotopes may be used in the methods of the present invention. A specific example isotope is technetium, more specifically $^{99m}$Tc. The solid form of technetium may be sodium pertechnate or any insoluble form of technetium produced during the electrolytic process described in PCT/AU2006/000554, e.g. insoluble oxichlorides. The technetium may be in the form of a radioactive isotope of technetium.

Other metallic radioisotopes or radionuclides may be utilised such as $^{198}$Au, $^{64}$Cu, $^{213}$Bi, $^{57}$Co, $^{51}$Cr, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y, $^{169}$Yb, $^{66}$Ga, $^{94m}$Tc, $^{89}$Zr and $^{192}$Ir.

For applications involving the loading of the particles and hence the 'labelling' of the synthetic polymer with an inactive progenitor of a radioisotope, any suitable inactive progenitor may be used. Typically, boron-10 ($^{10}$B) may be used.

As described in PCT/AU2006/000554, FibrinLite nanoparticles may be produced as a stable aqueous dispersion with a very low electrolyte concentration, less than the equivalent of 1.0 mM NaCl. Any of the methods described in PCT/AU2006/000554 or derivable therefrom for the preparation of the FibrinLite particles may be utilised in the preparation of the FibrinLite particles for use in the present invention. In the preferred methods described in PCT/AU2006/000554 this may be achieved by heating the isotope loaded graphite crucible at approximately 1600-1650° C. for 15 seconds to remove carrier sodium chloride before ablation of radioisotope above 2700° C. The boiling point of sodium chloride is only 1413° C., and the Tc-99m radioisotope is not volatile at this temperature. Where alternative radioisotopes (or inactive progenitors) are utilized in the methods of the invention the skilled addressee will be able to determine appropriate temperature of ablation, such as by reference to PCT/AU2006/000554.

Aqueous dispersions of FibrinLite nanoparticles made according to PCT/AU2006/000554 do not flocculate, precipitate or sediment on standing for e.g. 48 hours. The dispersion of nanoparticles may contain a very low (for example, in the range of about 1 micromolar to about 20 micromolar, typically about 10 micromolar) concentration of an anionic surfactant, typically sodium deoxycholate, which is compatible with and may be injected into, the blood circulation of a living subject. The FibrinLite nanoparticles may be stored in any appropriate manner, preferably to permit stability of the dispersion, such as by storage in a low concentration of a weakly acidic buffer, such as at a final concentration of 300 micromolar sodium dihydrogen citrate at pH 4.1. The dispersion of nanoparticles is stable, and may be size-fractionated by the use of readily available hydrophilic membrane filters, such as Millipore mixed cellulose ester (MCE) syringe filters, available with porosity of 800, 450 and 220 nm. More than 90% of the radioactivity in a typical FibrinLite nanoparticle preparation will pass through a 800 nm MCE filter, and the same preparation can be shown by thin-layer chromatography to contain typically less than 5% soluble isotope.

Conditions for Radiolabelling Synthetic Polymers Using FibrinLite Nanoparticles

The nanoparticles so-produced or obtained may be used in the methods of the present invention for radiolabelling of synthetic polymers.

Hydrophobic interfaces, such as an air-water interface, hydrocarbon-water interfaces and by inference probably a graphite-water interface as in aqueous FibrinLite suspensions, may generally attract a slight predominance of hydroxyl ions in pure water. The result is that these interfaces behave as slightly negatively charged, although the surface potentials are usually very low (tens of millivolts). In the case of FibrinLite, the nanoparticles may also bear increased negative charge on their surface due to adsorption of the anionic surfactant, typically deoxycholate, that may be used in their preparation. As the particles and a polymer surface are similarly charged in the same aqueous medium they may weakly repel each other at the nanometers scale when their charged diffuse double layers overlap. However if the pH is reduced, the concentration of hydroxyl ions will be reduced compared to pure water, thus decreasing the repulsive charges present at these interfaces. The inclusion of milli-molar concentrations of electrolyte or preferably of nano-molar concentrations of polycations very rapidly screens this potential such that it offers little energetic barrier to the adsorption and cohesion of particles to a polymer surface in these systems. Such screening, at Debye lengths<10 nm, will produce a situation in which attractive dispersion, ion correlation or hydrophobic forces will usually dominate the total interaction energy of these surfaces. The result is that particles once engaged with the polymer surface will tenaciously adhere to that surface in an essentially irreversible manner. The conditions thereby promote avid binding of the synthetic polymer and nanoparticle composite. In preferred embodiments the medium in which the contacting occurs may comprise an electrolyte concentration or pH, or combination thereof, which promote the short range attractive forces between the nanoparticles and synthetic polymer and suppress the long-range electrostatic repulsive forces leading to an overall attractive and adhesive interaction between the particles and the polymer surface. As a result of successful contacting the synthetic polymer may be described as being associated with or complexed with the nanoparticle composite. The resultant entity may also be referred to as a complex. It is noted that the terms "complex" and "complexed with" in the present context are not intended to imply any particular structural arrangement of the synthetic polymer and nanoparticle composite other than what occurs as a result of successful contacting in which they become tightly bound.

In the methods of the present invention the FibrinLite nanoparticles may be used to label a synthetic polymer by contacting the nanoparticles and the polymer under conditions of suitable electrolyte concentration and or pH. The inventors have discovered that suitable solution conditions of electrolyte concentration and or pH can be selected that facilitate the reduction of repulsive charges described above and thus enable short-range attractive forces to dominate over long-range electrostatic repulsive forces, such that the Fibrin-Lite nanoparticles become virtually irreversibly bound to a polymer surface. In view of the disclosure herein it will be appreciated that appropriate and, if desired, optimal, binding conditions, such as electrolyte including simple electrolytes and polycations, and pH, can be determined empirically for a desired contacting between nanoparticles and a synthetic polymer.

The contacting may occur in any suitable medium, although an aqueous medium will usually be preferred. Prior to the contacting the nanoparticles may be prepared in or stored in a suitable storage medium, generally selected to permit stability of the dispersion. Thus the dispersion of nanoparticles may contain a very low (for example, about 10 micromolar) concentration of an anionic surfactant, such as sodium deoxycholate. Prior to the contacting step of the method of the invention, the nanoparticles may be pre-treated to adjust the conditions of the dispersion to favor binding of the nanoparticles and synthetic polymer. For example, conditions such as buffer type, pH, electrolyte concentration and type, presence or absence of surfactant and concentration of any component, including of the nanoparticles, may be adjusted. Adjustment of the ionic strength of the medium may occur in the presence or absence of the synthetic polymer. Typically adjustment of the ionic strength of the medium, when in the presence of the nanoparticles, will occur in the presence also of the synthetic polymer so as to promote the binding between nanoparticles and the synthetic polymer, rather than binding only between nanoparticles that may ultimately cause aggregation and clumping.

The inventors have surprisingly discovered that under slightly acidic conditions of pH, for example pH 3.5, optimal binding of the FibrinLite particles to a synthetic polymer such as polypropylene or polystyrene occurs over a certain low range of simple electrolyte concentration, about 1 mM to about 25 mM, therein providing for avid binding to form a radiolabelled synthetic polymer. In one preferred aspect the inventors describe the specific conditions as an aqueous medium or solution comprising a simple electrolyte concentration of greater than about 1 millimolar and less than about 25 millimolar, with pH adjustment to below 4.5 and not less than 3.0. Typically, at higher pH, for example neutral pH, higher concentrations of simple electrolyte are used, such as greater than about 80 millimolar and less than about 150 mM. Further, the inventors discovered that optimal binding of the FibrinLite particles to a synthetic polymer such as polypropylene or polystyrene can be effectively induced even at neutral pH by very low concentrations of a polycation, such as poly-lysine.

The ability to influence the binding of the nanoparticles and synthetic polymer through the use of electrolyte and pH offers additional advantages. For example, the option to use a lower concentration of NaCl by using a pH of about 3.5 may be an advantage when radiolabelling a synthetic polymer or a device comprising a synthetic polymer that already carries another, weakly bound, ligand. In these circumstances the use of lower electrolyte concentration may limit or avoid leaching of the ligand.

The Examples herein indicate that binding of FibrinLite nanoparticles to a synthetic polymer may be achieved through the use of the simple electrolyte sodium chloride (NaCl), which is most effective in inducing avid binding of the nanoparticles to the synthetic polymer at concentrations of greater than about 1 mM NaCl and less than about 25 mM when the pH is about 3.5. At neutral pH higher concentrations of electrolyte are typically used, about 80 mM. As will be appreciated, in view of the disclosure herein, appropriate conditions for inducing avid binding of nanoparticles to a synthetic polymer may be achieved using any one or more of a large variety of electrolytes. The inventors describe herein that at pH 3.5 a simple electrolyte concentration of greater than about 1 millimolar may be used to induce avid binding of nanoparticles to a synthetic polymer and thus, where the nanoparticles have a radioactive particulate core, to provide for the preparation of a radiolabelled synthetic polymer. Generally, at pH 3.5 the simple electrolyte concentration of the solution or medium for the contacting is expected to be in the range of about 1 millimolar to about 100 millimolar; typically, about 1 millimolar to about 75 millimolar; about 1 millimolar to about 50 millimolar; about 1 millimolar to about 25 millimolar. More typically the electrolyte concentration of the solution is expected to be in the range of about 1 millimolar to about 150 millimolar; typically from about 1 millimolar to about 100 millimolar; from about 1 millimolar to about 50 millimolar; from about 2 millimolar to about 50 millimolar; from about 2 millimolar to about 40 millimolar; from about 2 millimolar to about 30 millimolar; from about 10 millimolar to about 30 millimolar; from about 10 millimolar to about 20 millimolar; about 15 millimolar. Higher concentrations, about 80 mM are typically used at neutral pH.

A person of skill in the art will understand that the ionic strength of an electrolyte solution or medium for the contacting step of the present invention may be achieved by, for example, using NaCl wherein a suitable ionic strength may be achieved with an NaCl concentration of about 15 mM or, for example, a $MgSO_4$ concentration of less than about 15 mM. A person of skill in the art will also understand that a suitable ionic strength of an electrolyte solution may be achieved by use of a number of different ionic species, for example a mixture of NaCl and $MgSO_4$. Furthermore a person of skill in the art will understand the ionic strength may be achieved by use of at least one ionic species and at least one non-ionic species such as an osmolyte or high molecular weight polymer such as polyethylene glycol. For example, where the effective concentration of water is reduced, the concentration of electrolyte may need to be increased.

Any suitable ionic species may be used in the methods of the invention. For example, the ionic species may be selected from the group comprising salts of Na, Ni, Al, Ru, Pt, Os, Ir, Fe, Se, Sn, K, Te, Mn, Mo, V, Mg, Zn, Ca, Cu, Co. For medical or veterinary use in living subjects the ionic species will typically be limited to those that are non-toxic at the effective concentrations, e.g. Na, K, Ca. The skilled addressee will understand that, in the absence of any other relevant changes to a given set of reaction conditions (for example in a contacting step), K used instead of Na would typically be used at the same concentration as Na, whilst Ca used instead of Na would typically be used at half the concentration as Na.

In addition the inventors have discovered that very low concentrations of polycationic species are particularly effective in inducing substantially irreversible FibrinLite nanoparticle binding to synthetic polymers, and that even at neutral pH the polycation effect is optimal at a low nanomolar range of concentrations rather than the millimolar concentrations used for simple electrolytes.

Polycations include, for example, polybrene (hexadimentrine bromide), protamine, aprotinin, polylysine, poly(ethyleneimine) (PEI), poly(diallyldimethylammonium chloride) (PDDA), poly(N-methyl-4-vinylpyridinium iodide), poly(allylamine hydrochloride), poly(butyl acrylate-co-N-methyl-4-vinylpyridinium iodide), poly(butadiene-co-N-methyl-4-vinylpyridinium) iodide, poly(styrene-co-4-vinylpyridine), poly(ethyl acrylate-co-4-vinylpyridine), polyaniline-based polymers, polypyrrole-base polymers. For medical or veterinary use in living subjects the ionic species will typically be limited to those that are non-toxic at the effective concentrations, e.g. protamine. Without wishing to be bound by theory the inventors presume that polycations induce this effect by efficiently shielding the negative electrostatic charges of hydroxyl and, where present, deoxycholate groups on the particle and polymer surfaces, enabling closer contact of the nanoparticles and thus dominance of short range attractive forces. Consistent with this presumption, polyanions do not have this effect, as they do not counter the negative charges of hydroxyl or deoxycholate groups.

The Examples herein indicate that binding of FibrinLite nanoparticles to polystyrene and polypropylene may be achieved through the use of the simple electrolyte sodium chloride (NaCl), which at pH 3.5 is particularly effective in inducing avid binding of the FibrinLite nanoparticles to the synthetic polymer at concentrations of greater than 1 mM. As indicated herein appropriate ionic strength conditions may be generated for the contacting step through the use of alternatives to the simple electrolyte NaCl. Accordingly it will be understood that alternative ionic species may be utilized at a concentration which corresponds to the ionic strength of a solution or medium defined by a stated concentration of NaCl. The electrolyte concentration in the contacting step may be any concentration in the range corresponding to greater than 1 mM NaCl to about 300 mM NaCl, such as from about 2 mM NaCl to about 250 mM NaCl, from about 3 mM NaCl to about 200 mM NaCl, from about 4 mM NaCl to about 150 mM NaCl, from about 5 mM NaCl to about 100 mM NaCl, from about 6 mM NaCl to about 75 mM NaCl, from about 7 mM NaCl to about 50 mM NaCl, from about 8 mM NaCl to about 30 mM NaCl, from about 9 mM NaCl to about 25 mM NaCl, from about 10 mM NaCl to about 20 mM NaCl, from about 11 mM NaCl to about 18 mM NaCl, from about 12 mM NaCl to about 15 mM NaCl. In preferred methods the electrolyte concentration in the contacting step may be any concentration in the range corresponding to about 5 mM NaCl to about 150 mM NaCl, for example an electrolyte concentration corresponding to about 15 mM NaCl, when the pH is 3.5, or about 80 mM when the pH is neutral.

The Examples herein indicate that binding of FibrinLite nanoparticles to synthetic polymers may be achieved through the use of the polycation polylysine of average molecular weight 20,000 or protamine, which are effective in inducing avid binding of the FibrinLite nanoparticles to polystyrene and polypropylene at concentrations of greater than about 5 nanomolar, and at neutral pH. As indicated herein appropriate conditions may be generated for the contacting step through the use of alternatives to the polycation polylysine. Where alternatives are used, the skilled addressee will be able to empirically determine appropriate conditions. For example, alternative polycationic species may be utilized at a concentration which corresponds to the shielding effect of a solution or medium defined by a stated concentration of polylysine. As guidance, the polycation concentration in the contacting step may be any concentration in the range corresponding to greater than about 5 nanomolar polylysine to about 500 nanomolar polylysine, about 10 nanomolar polylysine to about 300 nanomolar polylysine, such as from about 10 nanomolar polylysine to about 200 nanomolar polylysine, from about 15 nanomolar polylysine to about 150 nanomolar polylysine, from about 20 nanomolar polylysine to about 100 nanomolar polylysine, from about 25 nanomolar polylysine to about 75 nanomolar polylysine, from about 30 nanomolar polylysine to about 50 nanomolar polylysine. In preferred methods the polycation concentration in the contacting step may be any concentration in the range corresponding to about 10 nanomolar to about 100 nanomolar, for example a polycation concentration corresponding to about 30 nanomolar polylysine. As further illustrative, the Examples demonstrate effective binding in the presence of protamine. The polycation concentration in the contacting step may be thus be any concentration in the range corresponding to greater than about 1 microgram/ml protamine, such as in the range of about 1 microgram/ml to about 50 microgram/ml protamine, about 2 microgram/ml to about 20 microgram/ml protamine, such as from about 2 microgram/ml to about 15 microgram/ml protamine, or from about 2 microgram/ml to about 12 microgram/ml protamine. In more preferred embodiments the concentration is in the range of from about 3 microgram/ml to about 11 microgram/ml protamine, even more preferably from about 5 microgram/ml to about 10 microgram/ml protamine, such as about 9 microgram/ml protamine (corresponding to about 2000 nanomolar).

The contacting step may be undertaken in any suitable medium as may be determined by the skilled addressee, although preferably an aqueous medium will be used. Any suitable buffer, comprising electrolyte corresponding to greater than about 1 mM NaCl may be used. For example, the contacting step may be in an aqueous buffer comprising 500 micromolar sodium citrate and further comprising electrolyte corresponding to greater than about 1 mM NaCl.

The buffer used in the contacting step may be of any suitable pH. Preferably the buffer will be in the range from about pH 3.5 to about pH 8.5. As described herein the desired and optimal pH can be determined by the skilled addressee taking into account other reaction conditions, such as the electrolyte(s) type and concentration.

The contacting may comprise modification of the conditions during the course of the contacting, such as an increase or decrease in the temperature of incubation during the contacting, or an increase or decrease of agitation of the medium or mixing during the contacting.

The Examples herein demonstrate high avidity binding of the nanoparticles to polystyrene, polystyrene sulphonate and to polypropylene. On the basis of the description presented herein it will be apparent that the methods of the invention are applicable to radiolabelling of any synthetic polymer that presents in at least part of its surface a hydrophobic interface with water. It may present charged chemical groups, e.g. sulphonate to the water, but binding of nanoparticles can still occur if the surface (preferably the majority of the surface) is hydrophobic under the conditions used for contacting with FibrinLite. The inventors have demonstrated that even sulphonated polystyrene, displaying negatively charged sulphonate groups on its surface, behaved similarly to normal polystyrene in binding experiments with FibrinLite, thereby further demonstrating that similar binding occurs over a large variety of synthetic polymers.

The methods of the invention have particular application in the preparation of medical devices, such as implantable medical devices, for which a therapeutic or diagnostic benefit arises where the device is associated with a radioisotope, such as by having the device radiolabelled. Synthetic polymers are commonly used as preferred materials for implantable devices due to their non-thrombogenic and good mechanical properties. For example, polytetrafluorethylene (PTFE), expanded polytetraflourethylene (EPTFE) polyurethane are used in a variety of clinical applications as are polyvinyl chloride, polyamides, polystyrene and teflon. Synthetic polymers used for vascular grafts include polyester, for example polyethylene terepthalate, polyurethane, and polytetrafluorethylene, among others. For the purposes of this invention synthetic polymers include but are not limited to polystyrene, polypropylene, polytetrafluorethylene (PTFE), expanded polytetraflourethylene (EPTFE), polyurethane, polyvinyl chloride, polyamides, polystyrene, teflon, polyester, polyethylene terephthalate, poly(butylene terephthalate) (PBT), poly (ethylene oxide) (PEO), polylactide (PLA), polyglycolide (PGA), poly(lactide-co-glycolide) (PLGA), poly(e-caprolactone), polydioxanone, trimethylene carbonate, polyanhydride, poly[bis(p-carboxyphenoxy)propane:sebacic acid.

The synthetic polymer may be presented to the FibrinLite nanoparticles in the contacting step in any suitable form such as free, for example as a suspension or dispersion such as in the form of polymer microparticles or nanoparticles, in an attached form such as a polymer coating on a surface of e.g. a metal, or in an integrated form. To illustrate, a synthetic polymer in an "attached" form may also include the situation where the synthetic polymer is bound to a carrier, device or implant, such as a catheter or microparticle or microsphere. The attachment may be of any suitable form including direct binding of the synthetic polymer to the carrier, device or implant or it may be indirect, such as through one or more intermediary molecules or bonding agents. A synthetic polymer in an "integrated" form includes, for example, the situation where the synthetic polymer forms an integral part of a carrier, device or implant, such as a catheter, microparticle or microsphere. To illustrate, the Examples herein demonstrate binding of the nanoparticle composite to, and hence radiolabelling of, polystyrene microwells and polypropylene vials. In such cases the synthetic polymer may be considered as an "integrated" synthetic polymer. The synthetic polymer to be radiolabelled may be in the form of a coating or encapsulation of an entity such as a carrier, device or implant. The coating or encapsulation may be partial or it may be complete.

The synthetic polymer may be presented to the FibrinLite nanoparticles in the contacting step comprised in or on a catheter, a fibre, a rod or filament, a membrane, a wafer, a mesh or gauze, a porous sponge, a tube or stent, a bead or capsule or microparticles in the form of microparticles of known dimensions, a nanoparticle, a liposome.

Accordingly, a synthetic polymer may be contacted with, and hence labelled by, the carbon encapsulated nanoparticles (comprising a radioisotope or an inactive progenitor thereof) before being incorporated into or onto or otherwise being used for the preparation of a medical device, or the contacting may be after the synthetic polymer has been incorporated into or onto or otherwise been used for the preparation of a medical device, such that a medical device or a precursor thereof is used in the contacting.

The radiolabelled synthetic polymer (or synthetic polymer 'labelled' with an inactive progenitor of a radioisotope) may be used with or without one or more additional process steps. Where an additional step is implemented it may be simultaneously with the contacting or it may be subsequent to the contacting or, where multiple additional steps are implemented they may be a combination of additional steps simultaneously with the contacting and subsequent to the contacting. Where an additional step is implemented subsequent to the contacting, it may be in the presence of the same or a different media to that which was implemented for the contacting.

The radiolabelled synthetic polymer (or synthetic polymer 'labelled' with an inactive progenitor of a radioisotope) may be subjected to one or more purification steps subsequent to the contacting. This may comprise separation of radiolabelled synthetic polymer from unlabelled synthetic polymer and/or from free nanoparticle composite. In a typical reaction the contacting may result in satisfactory binding of nanoparticles to synthetic polymer to provide radiolabelled synthetic polymer, whilst retaining in the aqueous media of the contacting step unreacted components, typically a proportion of nanoparticles composite which have not become attached to synthetic polymer. Removal of unreacted components may be desirable, for example in circumstances where free nanoparticles composite would be detrimental, such as blood transport to non-target organs. The removal of unreacted components may be partial, substantially complete or complete. In this context "partial" removal will be understood to include removal of any amount of one or more unreacted or undesired components, more typically removal of up to about 80%, 90% or 95% of one or more unreacted or undesired components and "complete" removal will be understood to be removal of greater than about 95% of one or more unreacted or undesired components. Typically removal of at least 95% of unreacted or undesired components is preferred, more preferably removal of greater than about 96%, 97%, 98%, or 99% of unreacted or undesired components.

Hence it will be understood that reference to "purification" in this context is intended to mean any degree of purification, whereby the radiolabelled synthetic polymer (or synthetic polymer 'labelled' with an inactive progenitor of a radioisotope) after a "purification" step contains less impurities, such as unreacted components of the contacting, or other undesired components, compared to before the purification.

Any method capable of separating radiolabelled synthetic polymer (or synthetic polymer 'labelled' with an inactive progenitor of a radioisotope) from unreacted or undesired components, such as unbound radioactive nanoparticles, may be used in a purification step. For example, the method may comprise washing one or more undesired components away from the radiolabelled synthetic polymer, or may comprise extracting the radiolabelled synthetic polymer away from the one or more undesired components, or may comprise a combination of such steps. As an example, in the case where the polymer comprises microparticles, the beads may be retained on a porous support, while washing liquid is reticulated through the layer of microbeads on the support. Alternatively, the polymer particles may be sedimented by centrifugation from a bulk liquid, and the supernatant liquid decanted or aspirated off and replaced with more washing liquid until the desired degree of purification is attained.

In a typical protocol to radiolabel polystyrene microparticles (100-800 mg, 30 micron particle diameter), a fresh preparation of FibrinLite containing a suitable calculated amount of radioisotope (e.g. 10 mCi or 370 MBq) would first be treated with protamine (5-10 µg/mL) for 30 minutes at room temperature. The pretreated FibrinLite would then be added to prewashed microparticles and the mixture slowly rotated for 30 minutes at room temperature on an end-over-end mixer. The mixture would then be centrifuged to separate the microparticles from the unbound radioactive nanoparticles. The labeled microparticles would be further purified by resuspension in water or saline and separated once again by centrifugation. Where the polymer forms a larger bead, capsule or tube, a suitable amount of pretreated FibrinLite would be used to immerse the polymer to provide sufficient label after binding at room temperature for 1 hour and rinsing with water or saline.

The invention provides for the use of the radiolabelled synthetic polymer (or progenitor) for the manufacture of a medicament for the treatment of disease, such as cancer. In this context it will be understood that the medicament may include a medical device as described herein. The radiolabelled synthetic polymer may be incorporated or integrated into or onto an entity, such as a biological or non-biological entity, for example a carrier, device or implant, such as a catheter, microparticle, or nanoparticle. Typically, the radiolabelled synthetic polymer to be incorporated or integrated into or onto is free in solution, suspension or dispersion. The radiolabelled synthetic polymer may be caused to be attached to an entity, such as a biological or non-biological entity, for example a carrier, device or implant, such as a catheter or microparticle. The attachment may be by any suitable method compatible with retention of the radiolabel, including direct and indirect binding or attachment. The radiolabelled synthetic polymer may be used for coating or encapsulating of an entity such as a carrier, device or implant. The coating or encapsulation may be partial or it may be complete. The synthetic polymer may also be formed in situ at the anatomical site where therapy is intended, for example as a setting glue or gel. The form of the synthetic polymer may then be a nascent matrix formed in contact with the nanoparticles, in an aqueous medium.

Medical devices, such as implantable devices such as vascular grafts and stents, may include additional modifications such as are known in the art. For example, the devices may include a bio-active such as a bio-active coating, having anti-thrombogenic and/or anti-infective properties such as by inclusion of anti-thrombogenic agents, antibiotics, antibacterial agents or antiviral agents. The preparation of implantable devices having bio-active coatings is known in the art and is described, for example in U.S. Pat. No. 6,803,069 to Patnaik et al and entitled "Method for imparting a bio-active coating modified", the entire contents of which are herein incorporated by reference. As a further example, a medical device may include additional modifications which assist in targeting the device to a desired cell type, tissue, organ, or disease site. Such targeting ligands are known and include, for example, antibodies such as monoclonal antibodies specific to a receptor molecule expressed by the target cell type, tissue or organ or, for example over-expressed in a disease state. The targeting ligand may comprise a detectable label, such as a radioisotope. Targeting modifications also include polycations, such as polylysine which may be used to target the labelled synthetic polymer or device, for example to the lung of a subject.

The inventors describe herein methods by which avid binding of synthetic polymer and carbon encapsulated nanoparticle composites can be induced. The description herein is illustrated by reference to preferred embodiments and examples. On the basis of the description herein the skilled addressee will appreciate that where alternatives are used appropriate conditions may be determined empirically, such alternatives including the radioactive isotope or inactive progenitor thereof, the synthetic polymer(s), the electrolyte and the pH.

Pharmaceutical and/or Therapeutic Formulations

The present invention also provides pharmaceutical and therapeutic compositions of radiolabelled macromolecules, such as radiolabelled synthetic polymers, where the synthetic polymer is in association with a carbon encapsulated nanoparticle composite having a radioactive particulate core (FibrinLite). Typically, for medical use, salts of the compounds of the present invention will be pharmaceutically acceptable salts; although other salts may be used in the preparation of the inventive compounds or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, transdermal application, topical creams or gels or powders, or rectal administration. In one embodiment, the mode of administration is parenteral. In another embodiment, the mode of administration is oral. Depending on the route of administration, the formulation and/or compound may be coated with a material to protect the compound from the action of enzymes, acids and other natural conditions which may inactivate the therapeutic activity of the compound. The compound also may be administered parenterally or intraperitoneally.

Dispersions of compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

The compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound(s) of the invention, typically a radiolabelled synthetic polymer or polypeptide in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, antibacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier is an orally administrable carrier.

Another form of a pharmaceutical composition is a dosage form formulated as enterically coated granules, tablets or capsules suitable for oral administration.

Also included in the scope of this invention are delayed release formulations.

Compounds according to the invention also may be administered in the form of a "prodrug". A prodrug is an inactive form of a compound which is transformed in vivo to the active form. Suitable prodrugs include esters, phosphonate esters etc, of the active form of the compound.

In one embodiment, the compound of the invention may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the compounds and/or pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another embodiment, a compound of the invention may be administered in an amount in the range from about 100 to about 1000 mg per day, for example, about 200 mg to about 750 mg per day, about 250 to about 500 mg per day, about 250 to about 300 mg per day, or about 270 mg to about 280 mg per day.

Compounds in accordance with the present invention may be administered as part of a therapeutic regimen with other drugs. It may desirable to administer a combination of active compounds, for example, for the purpose of treating a particular disease or condition. Accordingly, it is within the scope of the present invention that two or more pharmaceutical compositions, at least one of which contains a compound of the invention, may be combined in the form of a kit suitable for co-administration of the compositions.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1

Binding of FibrinLite Dispersion to Polystyrene

Binding of a Tc-99m FibrinLite dispersion to a typical synthetic polymer was modeled using microwells of polystyrene, in a 96 well format that enabled individual radioactivity measurements of separated wells after binding and multiple washing steps (Nunc-Immuno™ LockWell™ modules). Citrate buffer (500 µM) was used at pH 3.5 and 6.0 to enable direct comparisons of the effect of pH on binding, at both very low and physiological electrolyte concentrations.

Diluted (1:10) Tc-99m FibrinLite was contacted with polystyrene microwells (100 µL/well) under various buffer conditions, namely 500 µM sodium citrate pH 3.5 (low electrolyte conditions);
(ii) 500 µM sodium citrate pH 3.5 plus 10 µM sodium deoxycholate (DOC);
(iii) 500 µM sodium citrate pH 3.5 plus 150 mM NaCl;
(iv) 500 µM sodium citrate pH 3.5 plus 10 µM sodium deoxycholate plus 150 mM NaCl;
(v) 500 µM sodium citrate pH 6.0 (low electrolyte conditions);
(vi) 500 µM sodium citrate pH 6.0 plus 10 µM sodium deoxycholate (DOC);
(vii) 500 µM sodium citrate pH 3.5 plus 150 mM NaCl; and
(viii) 500 µM sodium citrate pH 6.0 plus 10 µM sodium deoxycholate plus 150 mM NaCl.

Binding of particles was tested by incubating the microwells for 20 minutes at 37° C. with gentle agitation. The microwells were then rinsed five times with water before counting the radioactivity in individually separated wells.

As shown in FIG. 1a, the radioactive FibrinLite nanoparticles showed low binding to the polystyrene microwell surface at pH 3.5 and pH 6.0 under very low electrolyte conditions (500 micromolar sodium citrate); binding at pH 3.5 was a little better than at pH 6.0. However when 150 mM NaCl was included, binding increased 3.3 fold at pH 3.5 and 5.8 fold at pH 6.0, while the highest density of labelling was obtained with addition of electrolyte at pH 3.5 (see FIG. 1a). Thus binding of FibrinLite to a polymer such as polystyrene is optimal at slightly acid pH and with addition of an electrolyte.

Once bound, the particles are held with high avidity, as evidenced by the retention of radiolabel after multiple washes in the binding assay. Furthermore, addition of a low concentration of surfactant (10 µM sodium deoxycholate) reduced 5 fold the binding of FibrinLite to polystyrene found at pH 3.5 in the absence of electrolyte, but when the FibrinLite was bound together with 150 mM NaCl, the surfactant produced only a 4.2% drop in the higher binding produced at pH 3.5 (see FIG. 1a).

Figure 1B:
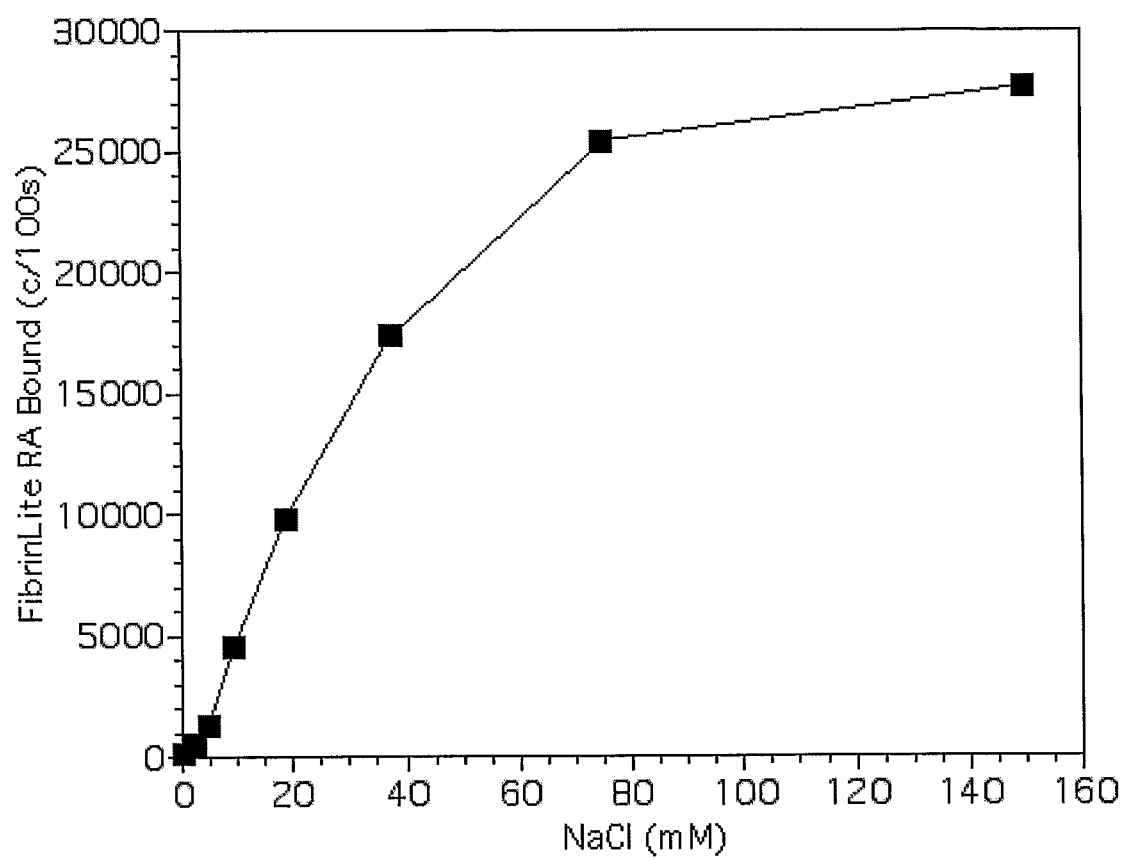
FIG. 1b: Binding of a Tc-99m FibrinLite dilution (1:10; 100 µL) to polystyrene microwells (Nunc Lockwells™) after pretreatment of the FibrinLite for 1 h at 20° C. with the concentrations of sodium chloride shown, in 0.5 mM Tris-acetate buffer pH 6.0.

In another experiment (FIG. 1b) the dose dependence of the effect of electrolyte was determined at neutral pH. A series of sodium chloride (NaCl) dilutions (500 µL) were first made in 0.5 mM Tris-acetate pH 6.5. The NaCl dilutions in the series were 0 mM, 2.34 mM, 4.69 mM, 9.38 mM, 18.75 mM, 37.5 mM, 75 mM and 150 mM. A Tc-99m FibrinLite preparation (55 µL) was then added to each NaCl dilution to give a final dilution of FibrinLite of 1:10, and the mixtures were stood at 20° C. for 1 h. Aliquots (100 µL) of each mixture were then dispensed onto polystyrene microwells (Nunc Lockwells™) and the microwells were incubated for 30 min at 37° C. with agitation. The polystyrene microwells were then rinsed 3 times with water before counting the bound radioactivity in each. As shown in FIG. 1b, maximum binding of FibrinLite to polystyrene at near neutral pH was apparent at greater than about 80 mM NaCl.

Example 2

Sodium Chloride Induced Binding of FibrinLite to Polypropylene Tubes and Polystyrene Lockwells at pH 3.5

A series of sodium chloride (NaCl) dilutions (500 µL) were first made in 0.5 mM sodium dihydrogen citrate buffer pH 3.5, contained in polypropylene tubes (Eppendorf; 1.5 mL capacity). The NaCl dilutions in the series were 0 mM, 2.34 mM, 4.69 mM, 9.38 mM, 18.75 mM, 37.5 mM, 75 mM and 150 mM. A Tc-99m FibrinLite preparation (55 µL) was then added to each NaCl dilution to give a final dilution of Fibrin-Lite of 1:10, and the mixtures then stood in the polypropylene tubes at 20° C. for 1 h. Aliquots (100 µL) of each mixture were then dispensed onto polystyrene microwells (Nunc Lockwells™) and the microwells were incubated for 30 min at 37° C. with agitation. The polypropylene tubes and the polystyrene microwells were then rinsed 3 times with water before counting the bound radioactivity in each.

Figure 2A:
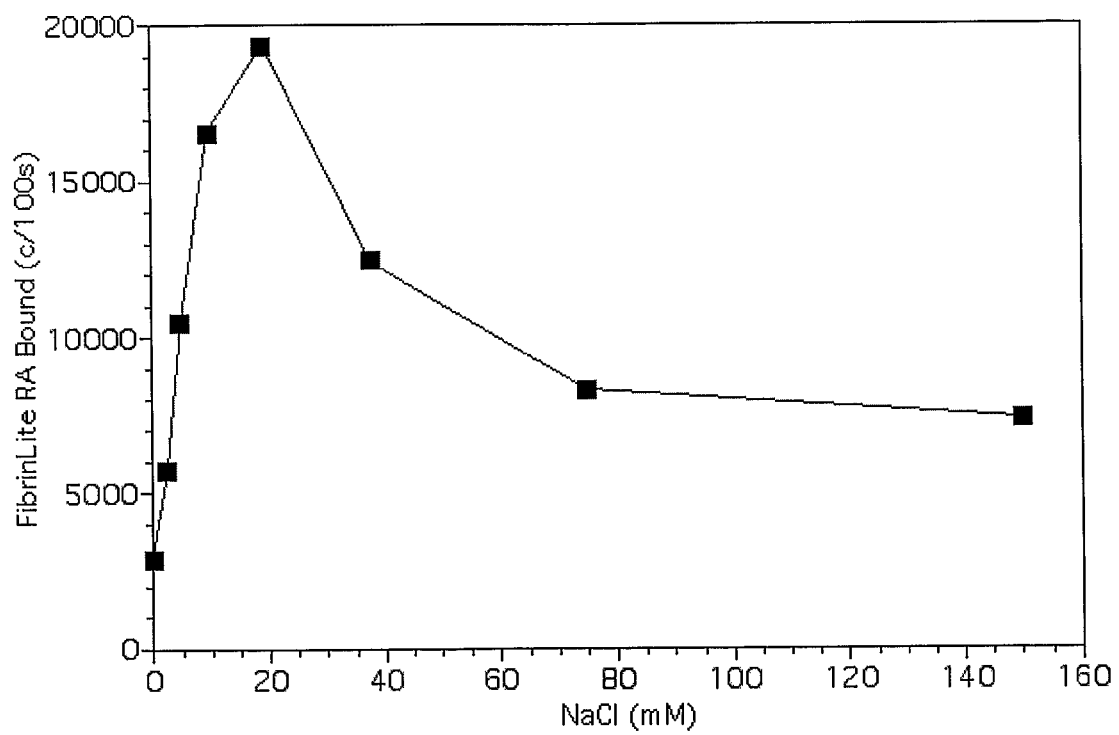
FIG. 2a: Binding of a Tc-99m FibrinLite dilution (1:10; 100 µL) to polystyrene microwells (Nunc Lockwells™) after pretreatment of the FibrinLite for 1 h at 20° C. with the concentrations of sodium chloride shown, in 0.5 mM sodium dihydrogen citrate buffer pH 3.5.
Figure 2B:
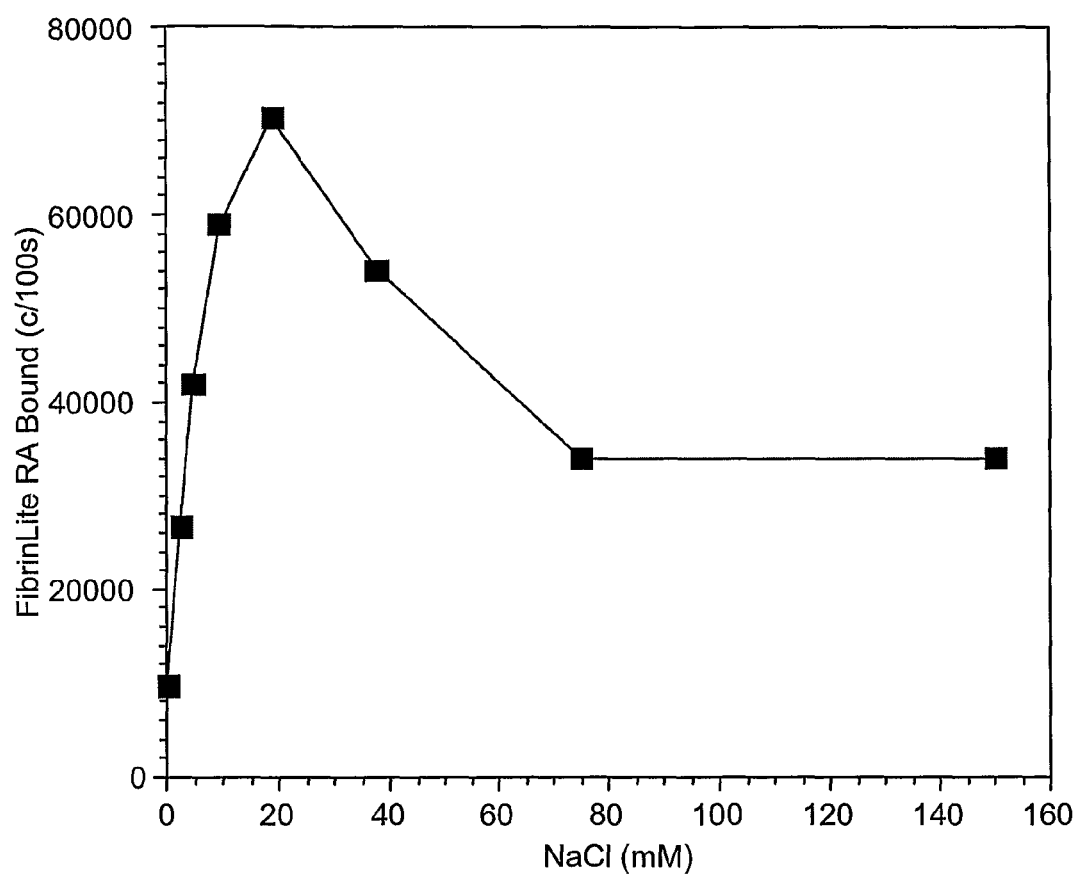
FIG. 2b: Binding of a Tc-99m FibrinLite dilution (1:10; 100 µL) to polypropylene vials (Eppendorf tubes) after pretreatment of the FibrinLite for 1 h at 20° C. with the concentrations of sodium chloride shown, in 0.5 mM sodium dihydrogen citrate buffer pH 3.5.

This experiment demonstrates that treatment with simple electrolytes under suitable conditions can markedly change the surface properties of FibrinLite nanoparticles, so that their binding to a polystyrene or polypropylene surface is strongly enhanced (FIG. 2a and FIG. 2b). Surprisingly, binding at pH 3.5 is not a simple function of electrolyte concentration, exhibiting a pronounced maximum at approximately 15 mM for binding to both polymers, while at physiological saline concentration (150 mM NaCl) binding was only approximately 35% (polystyrene) to 50% (polypropylene) optimal (FIGS. 2a and 2b, respectively). Thus compared to the effect of NaCl at neutral pH (FIG. 1b, above), considerably less electrolyte is needed to induce binding of FibrinLite at pH 3.5. The option to use a lower NaCl concentration at pH 3.5 may be an advantage in radiolabelling some devices comprising synthetic polymers that already carry another weakly bound ligand. In this case leaching of the other ligand can be limited or avoided with the lower electrolyte concentration.

Example 3

FibrinLite Binding to a Polymer after Albumin Pretreatment—Competition Binding

Diluted Tc-99m FibrinLite (1:10; 100 µL) was contacted to polystyrene microwells (Nunc Lockwells™) after pretreatment of the FibrinLite for 30 min at 20° C. with various concentrations of rabbit serum albumin (RSA; Sigma A0764), in a buffer containing 150 mM sodium chloride and 0.5 mM sodium dihydrogen citrate buffer pH 3.5. The concentrations of RSA used were 0, 15.6 µg/mL, 31.3 µg/mL, 62.5 µg/mL, 125 µg/mL, 250 µg/mL, 500 µg/mL and 1000 µg/mL. Binding on the polystyrene microwells was allowed for 30 min at 37° C. with agitation. The wells were then rinsed 5 times with water before individual wells were detached and the bound radioactivity counted.

Figure 3:
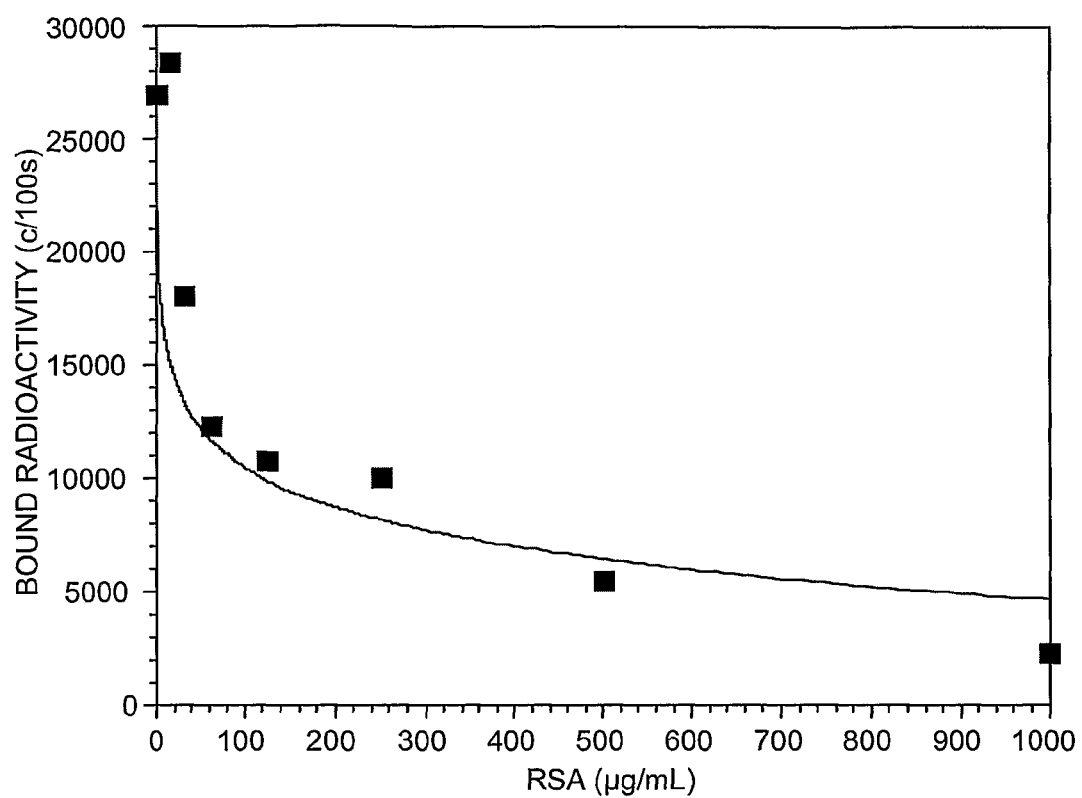
FIG. 3: Binding of a Tc-99m FibrinLite dilution (1:10; 100; µL) to polystyrene microwells (Nunc Lockwells™) after pretreatment of the FibrinLite for 30 min at 20° C. with the concentrations of rabbit serum albumin (RSA; Sigma A0764) shown, in a buffer containing 150 mM sodium chloride and 0.5 mM sodium dihydrogen citrate buffer pH 3.5.

This experiment demonstrates that the change in surface properties of FibrinLite induced by addition of electrolyte causes binding to both a protein and polystyrene, and that competition for binding sites occurs when both potential ligands are present together (FIG. 3). When the concentration of albumin is 1 mg/mL, it can almost extinguish the FibrinLite binding to polystyrene. This experiment also indicates that under these conditions FibrinLite binds to both albumin and polystyrene through a similar hydrophobic interaction.

Example 4

Retention of Bound FibrinLite on Polystyrene

FibrinLite was diluted (1:10) with 15 mM sodium chloride in 0.5 mM Tris-acetate buffer pH 6 and aliquots (100 µL) were dispensed on 16 microwells made of polystyrene (Nunc Lockwells™). Binding was allowed to occur for 1 hr at 37° C. with agitation, and then all wells were rinsed 5 times with water. Quadruplicate wells were then dried (control), or treated for 1 hr at 37° C. with agitation after addition of 100 µL water, saline (150 mM NaCl), or rabbit plasma. Finally, all wells were rinsed with water and the radioactivity counted.

Figure 4:
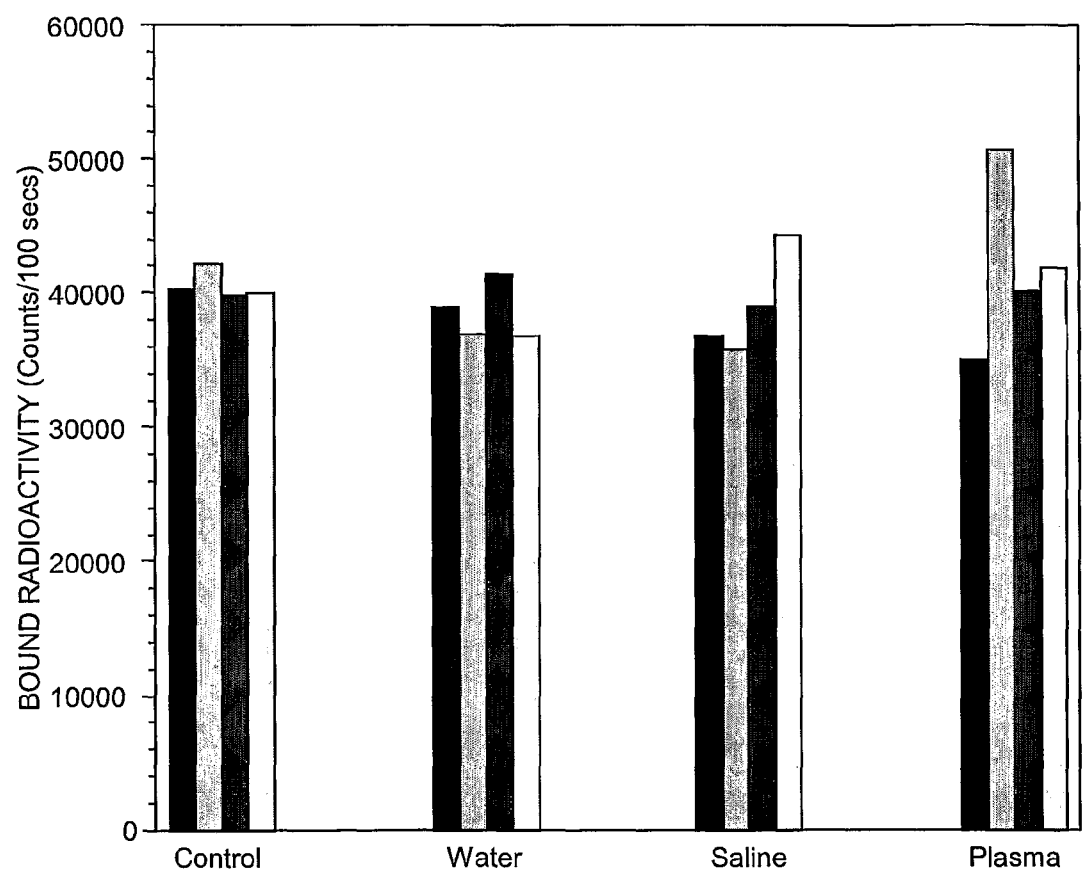
FIG. 4: Retention of bound Tc-99m FibrinLite on polystyrene microwells (Nunc Lockwells™) after washing with agitation for 1 hr at 37° C. in water, saline (150 mM NaCl), or rabbit plasma. "Control" samples were not subjected to post-binding washing with agitation. Results of quadruplicate microwells are shown.

This experiment demonstrates that once bound to polystyrene under appropriate conditions, FibrinLite is strongly adherent to the polymer surface, and treatment with the variety of biologically relevant solutions shown is not able to displace a significant amount of the bound FibrinLite radioactivity (FIG. 4). Once formed, the cohesive interaction between the FibrinLite nanoparticles and the polymer is very stable.

Example 5

Polycation Induced Binding of FibrinLite to Polymers

Tc-99m FibrinLite (1:10 dilution) was pretreated for 1 h at 20° C. with various concentrations of poly-D-lysine (MW 15-30 kd; Sigma 4408), namely 0, 0.078 µg/mL, 0.156 µg/mL, 0.313 µg/mL, 0.625 µg/mL, 1.25 mg/mL, 2.5 µg/mL and 5 µg/mL, in 0.5 mM Tris-acetate buffer pH 6. The pretreated FibrinLite was dispensed (100 µL/well) onto polystyrene microwells (Nunc Lockwells™) and binding allowed for 30 mM at 37° C. with agitation. The wells were rinsed 5 times with saline before individual wells were detached and the bound radioactivity counted.

Figure 5A:
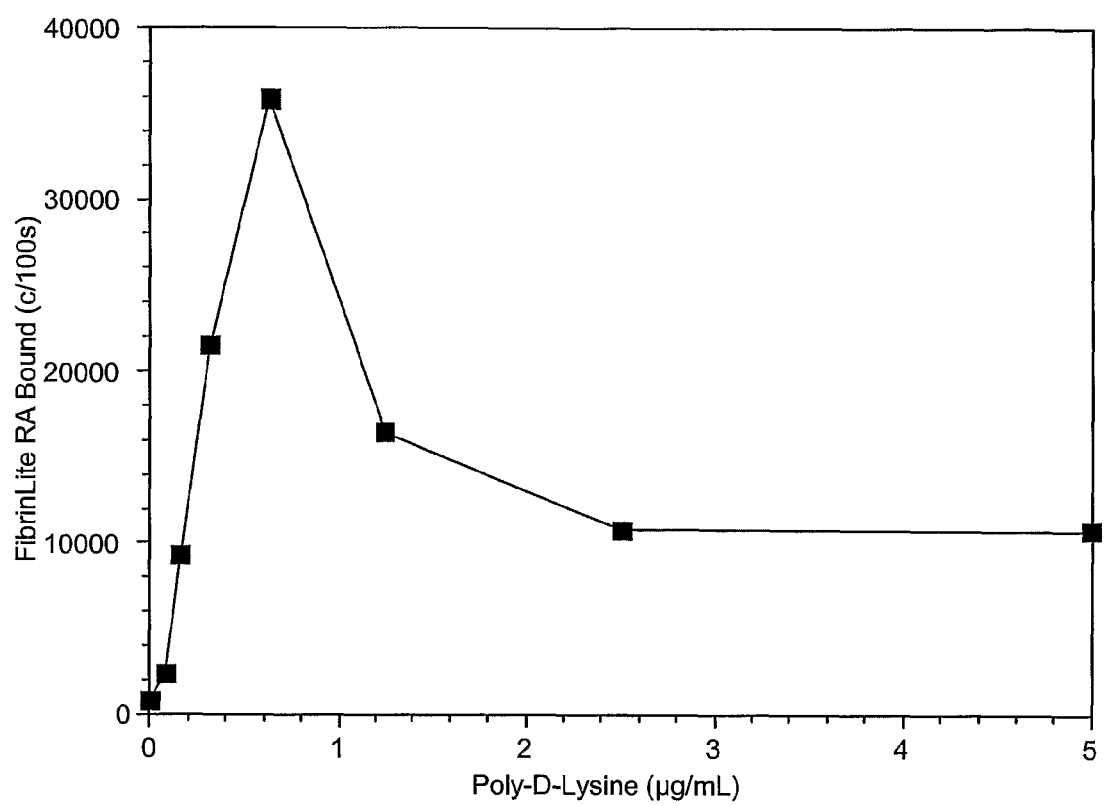
FIG. 5a: Polycation induced binding of FibrinLite to polystyrene. Binding of a Tc-99m FibrinLite dilution (1:10; 100 µL) to polystyrene microwells (Nunc Lockwells™) after pretreatment of the FibrinLite for 1 h at 20° C. with the concentrations of poly-D-lysine (MW 15-30 kd; Sigma 4408) shown, in 0.5 mM Tris-acetate buffer pH 6.

This experiment shows that treatment with very low concentrations of a typical polycation under suitable conditions can dramatically change the surface properties of FibrinLite nanoparticles, so that their binding to a polystyrene surface is markedly enhanced (FIG. 5a). Surprisingly, this binding is not a simple function of polycation concentration, exhibiting a pronounced maximum at approximately 0.6 µg/mL poly-D-lysine (30 nM), while binding was only approximately 30% optimal at 5.0 µg/mL poly-D-lysine. The results also demonstrate that the binding induced is not a simple charge interaction, as it is not reversed by several rinses with saline.

Figure 5B:
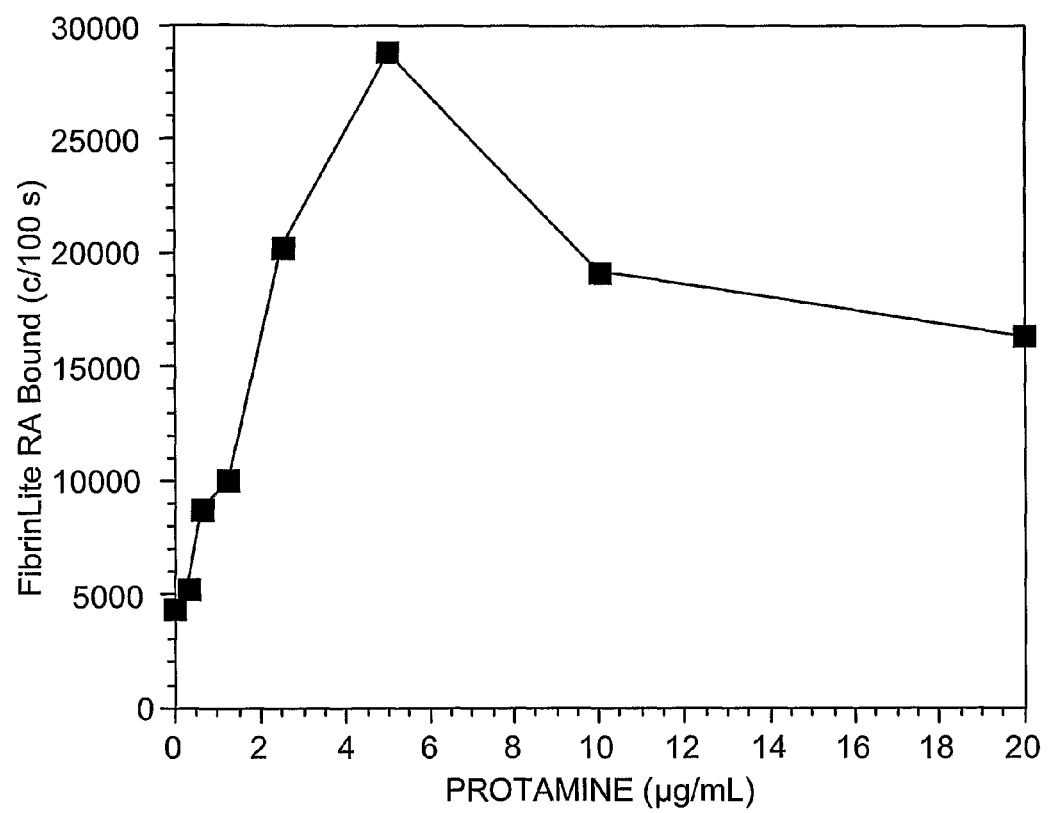
FIG. 5b: Polycation induced binding of FibrinLite to polystyrene. Binding of a Tc-99m FibrinLite dilution (1:10; 100 µL) to polystyrene microwells (Nunc Lockwells™) after pretreatment of the FibrinLite for 1 h at 20° C. with the concentrations of protamine sulphate (Sigma P4505) shown, in 0.5 mM Tris-acetate buffer pH 6.

A similar experiment is shown in FIG. 5b, this time using a different polycation, protamine, which is used clinically for reversal of heparin anti-coagulation. A series of protamine sulphate (Sigma P4505) dilutions (500 µL) were first made in 0.5 mM Tris-acetate buffer pH 6.0. The protamine dilutions in the series were 0, 0.32 µg/mL, 0.625 µg/mL, 1.25 µg/mL, 2.5 µg/mL, 5.0 µg/mL, 10 µg/mL and 20 µg/mL. A Tc-99m FibrinLite preparation (55 µL) was then added to each protamine dilution to give a final dilution of FibrinLite of 1:10, and the mixtures then stood for 20° C. for 1 h. Aliquots (100 µL) of each mixture were then dispensed onto polystyrene microwells (Nunc Lockwells™) and the microwells were incubated for 30 min at 37° C. with agitation. Aliquots (100 µL) were also dispensed into polypropylene Eppendorf tubes and these were stood 30 min at 20° C. The polystyrene microwells and the polypropylene tubes were then rinsed 3 times with water before counting the bound radioactivity in each.

Figure 5C:
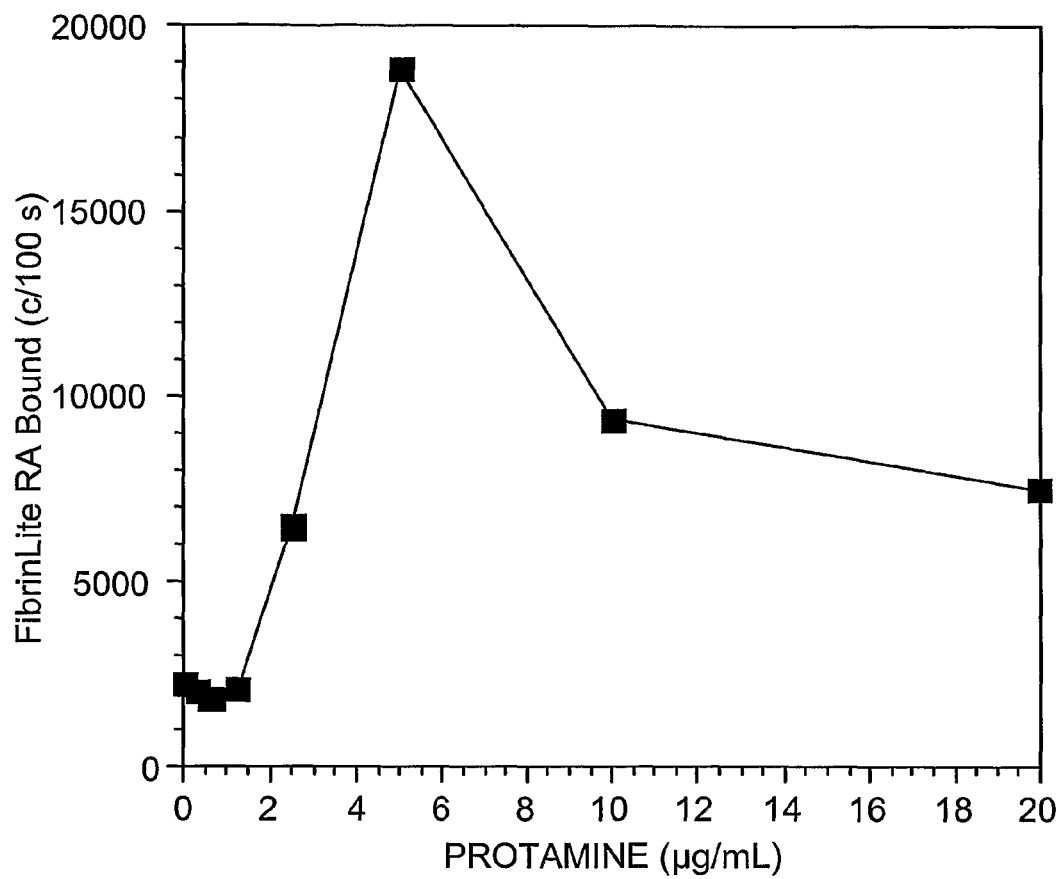
FIG. 5c: Polycation induced binding of FibrinLite to polypropylene. Binding of a Tc-99m FibrinLite dilution (1:10; 100 µL) to polypropylene vials (Eppendorf tubes) after pretreatment of the FibrinLite for 1 h at 20° C. with the concentrations of protamine sulphate (Sigma P4505) shown, in 0.5 mM Tris-acetate buffer pH 6.

As shown in FIG. 5b, protamine was effective in inducing FibrinLite binding to polystyrene, and also induced binding to polypropylene (FIG. 5c). Once again, binding was not a simple function of polycation concentration, exhibiting a pronounced maximum at approximately 5 µg/mL protamine (approximately 1000 nanomolar) for both polystyrene and polypropylene.

Thus induction of binding was demonstrated for two different polycations and for binding to two different synthetic polymers. In all cases there exists a certain range of polycation concentration that is optimal, that can be determined for each polycation, for example in the manner described herein. However this optimal concentration appears to be independent of the type of polymer surface, and thus more to do with the shielding of electrostatic charges on the nanoparticles due to hydroxyl ions and deoxycholate.

Example 6

Effect of Polycation Molecular Weight on Binding of FibrinLite to Polymers

Tc-99m FibrinLite (1:10 dilution) was pretreated for 1 h at 20° C. with various concentrations of three different poly-D-lysines (A: MW 30-70 kd, Sigma P7886; B: MW 15-30 kd, Sigma 4408; C: MW 4-15 kd, Sigma P6403), namely 0, 0.25 µg/mL, 0.5 µg/mL, 1.0 µg/mL, 2.0 µg/mL, and 4.0 µg/mL, in 0.5 mM Tris-acetate buffer pH 6. The pretreated FibrinLite was dispensed (100 µL/well) onto duplicate polystyrene microwells (Nunc Lockwells™) and binding allowed for 30 min at 37° C. with agitation. The wells were rinsed 5 times with saline before the plate was imaged under a Siemens Diacam gamma camera.

Figure 6:
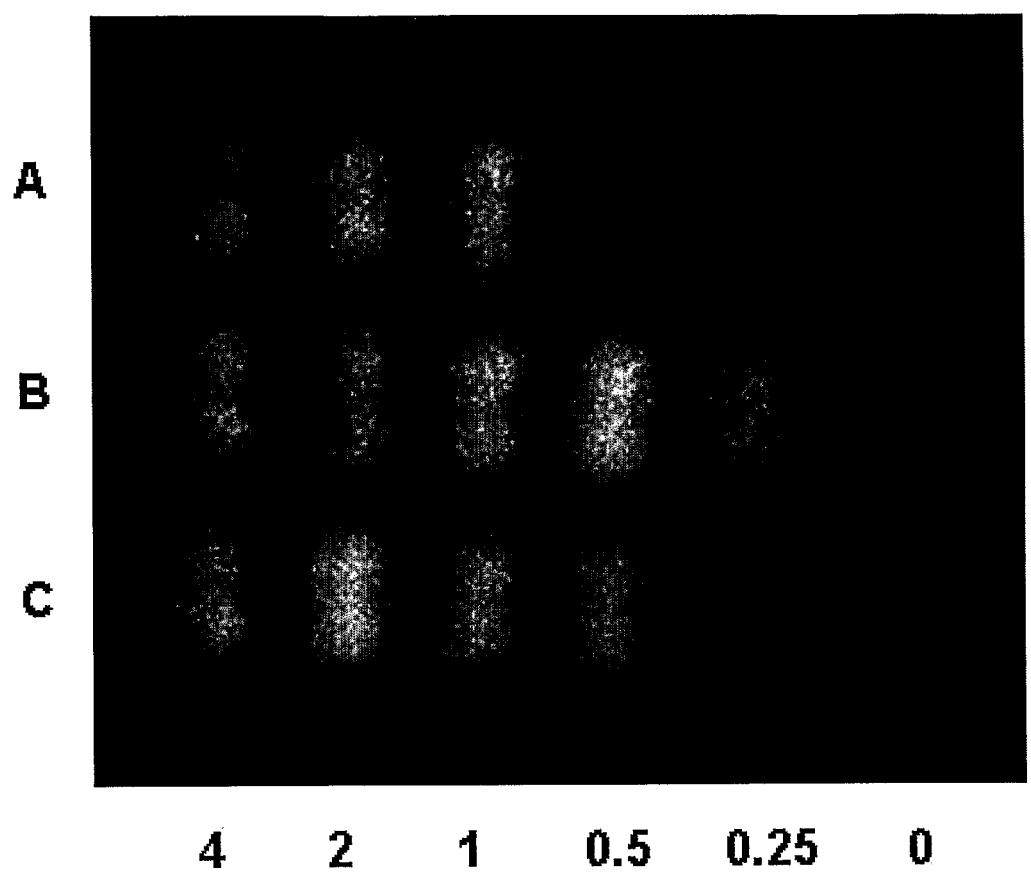
FIG. 6: Binding of Tc-99m FibrinLite nanoparticles to polystyrene microwells induced by pre-treatment of the FibrinLite with three different molecular size fractions of poly-D-lysine. The figure shows a gamma camera image of the bound nanoparticles in duplicate wells, and the concentrations (µg/mL) of the three different poly-D-lysines used; A—molecular weight 30-70 kd, B—molecular weight 15-30 kd, and C—molecular weight 4-15 kd.

This experiment shows that polycation enhancement of FibrinLite binding to polystyrene is dependent on both the concentration and the molecular size of the polycation (FIG. 6). Surprisingly, this binding is not a simple function of polycation molecular size; poly-D-lysine of molecular weight 15-30 kd was effective at lower concentrations than poly-D-lysine of molecular weight 4-15 kd, but also effective at lower concentrations than poly-D-lysine of molecular weight 30-70 kd (FIG. 6).

Example 7

Binding of Tc-99m FibrinLite to Microspheres of Sulphonated Polystyrene (Aminex 50W-X4; Bio-Rad)

Figure 7:
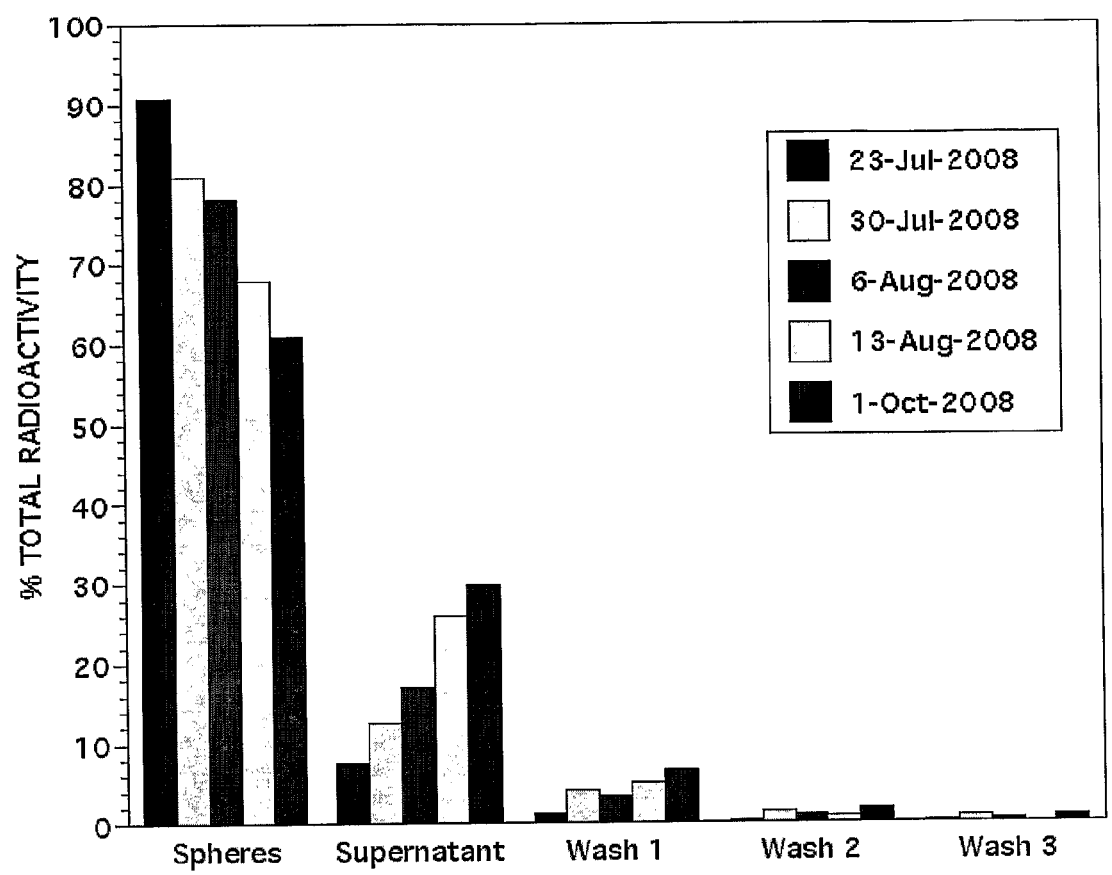
FIG. 7: Binding of Tc-99m FibrinLite to microspheres of sulphonated polystyrene (Aminex 50W-X4; Bio-Rad) induced by pre-treatment of the FibrinLite with a polycation, protamine sulphate (Sigma P4505). The graph shows the distribution of Tc-99m radioactivity between the final microsphere preparation (spheres), the residue in the labelling incubation after completion of label uptake (supernatant) and in the three washings of the labelled microspheres (wash 1, 2 and 3). The results are shown for five independent preparations (different colours), in which the Tc-99m FibrinLite preparation was changed by reducing the crucible ablation temperature over the range 2,800° C. to 2,600° C. Reduction in temperature was associated with reduction in bound label.

Tc-99m FibrinLite (2-5 mCi) was pretreated for 30 min at 20° C. with protamine sulphate (10 µg/mL; Sigma P4505) in water (6.0 mL). The pretreated FibrinLite was then added to a slurry of prewashed (3× with water) microspheres of average diameter 30 microns (Aminex 50W-X4; Bio-Rad; 100 mg), and the suspension gently mixed for 30 mins at 20° C. The microspheres were then separated from the soluble phase by brief centrifugation (5,000 rpm for 1 min) and the microspheres were resuspended and rinsed three times with water (5.0 mL). The radioactivity of the original soluble phase, the three wash supernatants and the final microsphere preparation were all counted and expressed as a percentage of the total Tc-99m radioactivity as shown in FIG. 7. The results are shown for five independent preparations (different colours), in which the Tc-99m FibrinLite preparation was changed by systematically reducing the crucible ablation temperature over the range 2,800° C. to 2,600° C. Reduction of temperature was associated with a reduction of bound label on the microparticles.

This experiment showed that pre-treatment of Tc-99m FibrinLite with a polycation (protamine) enabled subsequent labelling of sulphonated polystyrene microspheres with Tc-99m FibrinLite in such a way that the label was retained through extensive washing. The microspheres so-labeled can be separated and washed to provide a purified product suitable for in vivo gamma camera imaging investigations employing such biologically compatible microspheres. Protamine was chosen, as it is already in extensive clinical use as an antagonist of heparin. It was surprising that sulphonated polystyrene could be labelled with Tc-99m FibrinLite using the same method as for unsubstituted polystyrene; sulphonation did not change the ability of FibrinLite to bind, and thus illustrates the generality of the method for use with different synthetic polymers.

Example 8

Binding of Ga-67 FibrinLite to Microspheres of Sulphonated Polystyrene (Aminex 50W-X4; Bio-Rad)

Figure 8:
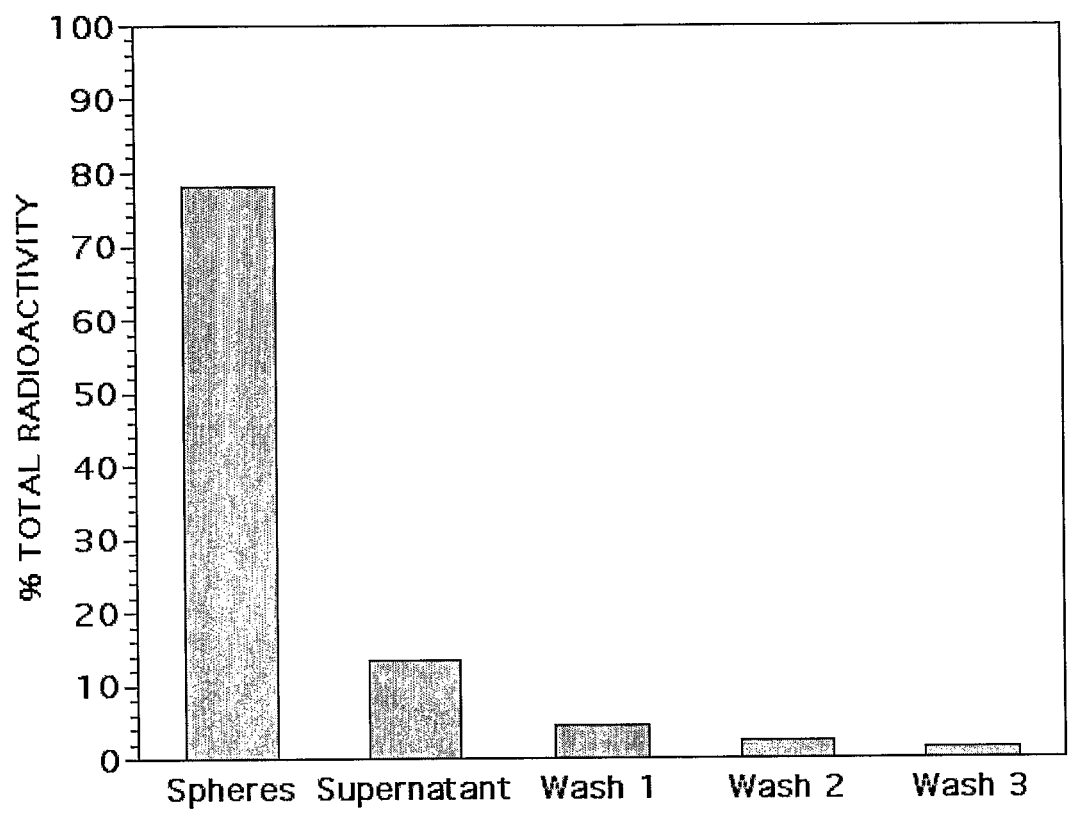
FIG. 8: Binding of Ga-67 FibrinLite to microspheres of sulphonated polystyrene (Aminex 50W-X4; Bio-Rad) induced by pre-treatment of the FibrinLite with a polycation, protamine sulphate (Sigma P4505). The graph shows the distribution of Ga-67 radioactivity between the final microsphere preparation (spheres), the residue in the labelling incubation after completion of label uptake (supernatant) and in the three washings of the labelled microspheres (wash 1, 2 and 3).
Figure 9:
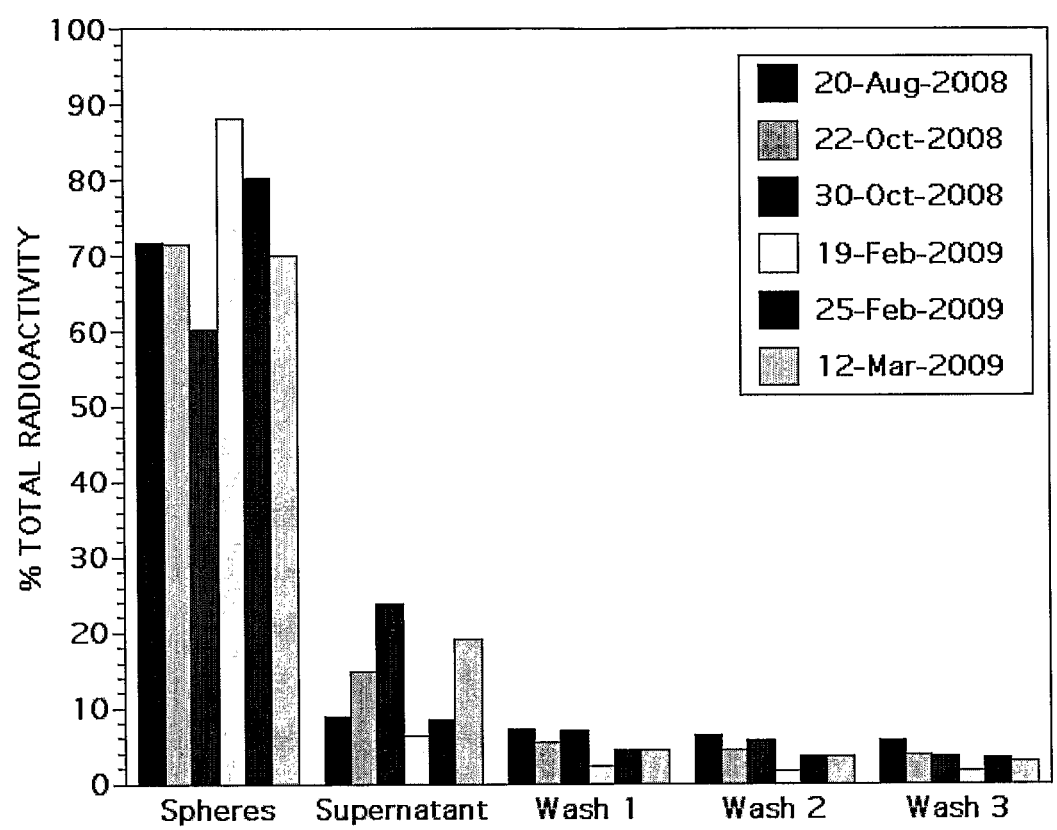
FIG. 9: Binding of Tc-99m FibrinLite to SIR-Spheres® (SIR-Spheres® is a Registered Trademark of Sirtex SIR-Spheres Pty Ltd) microspheres induced by pre-treatment of the FibrinLite with a polycation, protamine sulphate (Sigma P4505). The graph shows the distribution of Tc-99m radioactivity between the final microsphere preparation (spheres), the residue in the labelling incubation after completion of label uptake (supernatant) and in the three washings of the labelled microspheres (wash 1, 2 and 3). Results are shown for six independent preparations.

Ga-67 (200 MBq) as gallium chloride was obtained as a cyclotron product (ANSTO Radiopharmaceuticals and Industrials, Lucas Heights, Sydney), evaporatively loaded into a graphite micro-crucible, and plasma ablated essentially as described in PCT/AU2006/000554, but with omission of the preheating step at 1650° C. The resulting aerosol was collected with the Browitt precipitator described in U.S. Pat. No. 5,228,444, using 3.0 mL of 10 µM sodium deoxycholate as collecting fluid and conditions as described in PCT/AU2006/000554. The resulting Ga-67 FibrinLite (0.9 mCi) was pretreated for 30 min at 20° C. with protamine sulphate (10 µg/mL; Sigma P4505) in water (6.0 mL). The pretreated Ga-67 FibrinLite was then added to a slurry of prewashed (3× with water) microspheres of average diameter 30 microns (Aminex 50W-X4; Bio-Rad; 100 mg), and the suspension gently mixed for 30 mins at 20° C. The microspheres were then separated from the soluble phase by brief centrifugation (5,000 rpm for 1 min) and the microspheres were resuspended and rinsed three times with water (5.0 mL). The radioactivity of the original soluble phase, the three wash supernatants and the final microsphere preparation were all counted and expressed as a percentage of the total Ga-67 radioactivity as shown in FIG. 8.

This experiment shows that treatment of Ga-67 FibrinLite with a polycation under suitable conditions can also induce tight binding of Ga-67 FibrinLite nanoparticles to microspheres of a sulphonated polymer, and the Ga67 FibrinLite labeled microspheres can be separated and washed to provide a purified product suitable for in vivo gamma camera imaging investigations employing such biologically compatible microspheres. Since another isotope of gallium, e.g. Ga-68 behaves chemically the same as the Ga-67 isotope, it is concluded that Ga-68 FibrinLite can also be made by these methods and used as an imaging label, in the case of Ga-68 for Positron Emission Tomography (PET imaging).

Example 9

Binding of Tc-99m FibrinLite to SIR-Spheres Microspheres

The SIR-Spheres microspheres used in this example had been aged over more than 100 half-life equivalents of the Y-90 therapeutic isotope ($t_{1/2}$=64 hours), so as to provide a "cold" SIR-Spheres microspheres sample for labelling with imaging isotope. Tc-99m FibrinLite (2-5 mCi) was pretreated for 30 min at 20° C. with protamine sulphate (10 µg/mL; Sigma P4505) in water (6.0 mL). The pretreated FibrinLite was then added to a slurry of prewashed (3× with water) SIR-Spheres microspheres (100 mg) of average diameter 30 microns, and the suspension gently mixed for 30 mins at 20° C. The SIR-Spheres microspheres were then separated from the soluble phase by brief centrifugation (5,000 rpm for 1 min) and the SIR-Spheres microspheres were resuspended and rinsed three times with water (5.0 mL). The radioactivity of the original soluble phase, the three wash supernatants and the final labelled SIR-Spheres microspheres preparation were all counted and expressed as a percentage of the total Tc-99m radioactivity as shown in FIG. 7. The results are shown for six independent preparations (different colours).

This experiment shows that treatment of Tc-99m Fibrin-Lite with a polycation under suitable conditions can also induce tight binding of the Tc-99m FibrinLite nanoparticles to a specific type of polymer microsphere used in selective internal radiation therapy (SIRT) for cancer patients, and the SIR-Spheres microspheres so-labelled can be separated and washed to provide a purified product suitable for in vivo gamma camera imaging investigations of the biodistribution of therapeutic SIR-Spheres microspheres.

Example 10

Figure 10A:
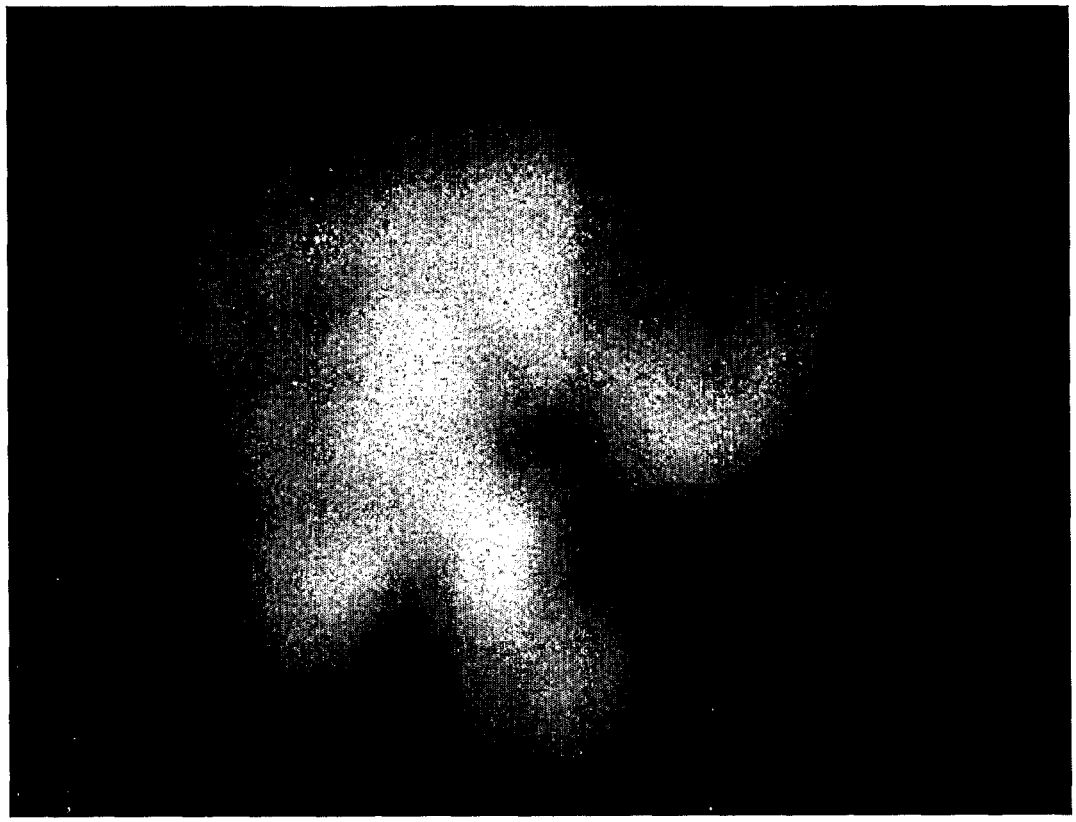
FIG. 10a: Gamma camera image of Tc-99m FibrinLite biodistribution in an excised rabbit liver after regional arterial instillation under anaesthesia. Note the distribution of label throughout the tissue of all lobes of the excised organ.

Imaging of Tc-99m FibrinLite Nanoparticles Following Instillation in the Arterial Vasculature of a Rabbit Liver A New Zealand white rabbit was anaesthetised with isoflurane and the cystic and hepatic arteries exposed. A vinyl microcatheter was inserted in the cystic artery and successive small aliquots of Tc-99m FibrinLite (total 3.8 mCi) was slowly instilled so that the hepatic artery flow carried the nanoparticles into the liver. Gamma camera imaging of the whole rabbit confirmed that labelled nanoparticles were rapidly taken up by the liver, but some label continued into the general circulation. After 60 min the rabbit was euthenased and the whole liver excised. Gamma camera imaging of the liver ex vivo (FIG. 10a) confirmed distribution of the labelled nanoparticles throughout all the tissue of the liver.

Figure 10B:
FIG. 10b: Gamma camera image of the body of the rabbit after removal of the liver shown in FIG. 10a above. Note the prominent uptake of labelled nanoparticles also in spleen and bone marrow.

This control experiment showed that the normal fate of Tc-99m FibrinLite nanoparticles following arterial instillation in the liver is to distribute throughout the whole tissue of the organ. Since the particles are of average diameter approx 300 nm, they can enter the smallest capillaries of all the tissue, where they are taken up by the phagocytic Kuppfer cells, part of the reticuloendothelial system (RES). This uptake is very rapid and efficient, but labelled nanoparticles also escape into the general circulation, from where they are taken up by the RES in the spleen and bone marrow of the rabbit, and some label can also be found in the kidneys (FIG. 10b).

Example 11

Figure 11A:
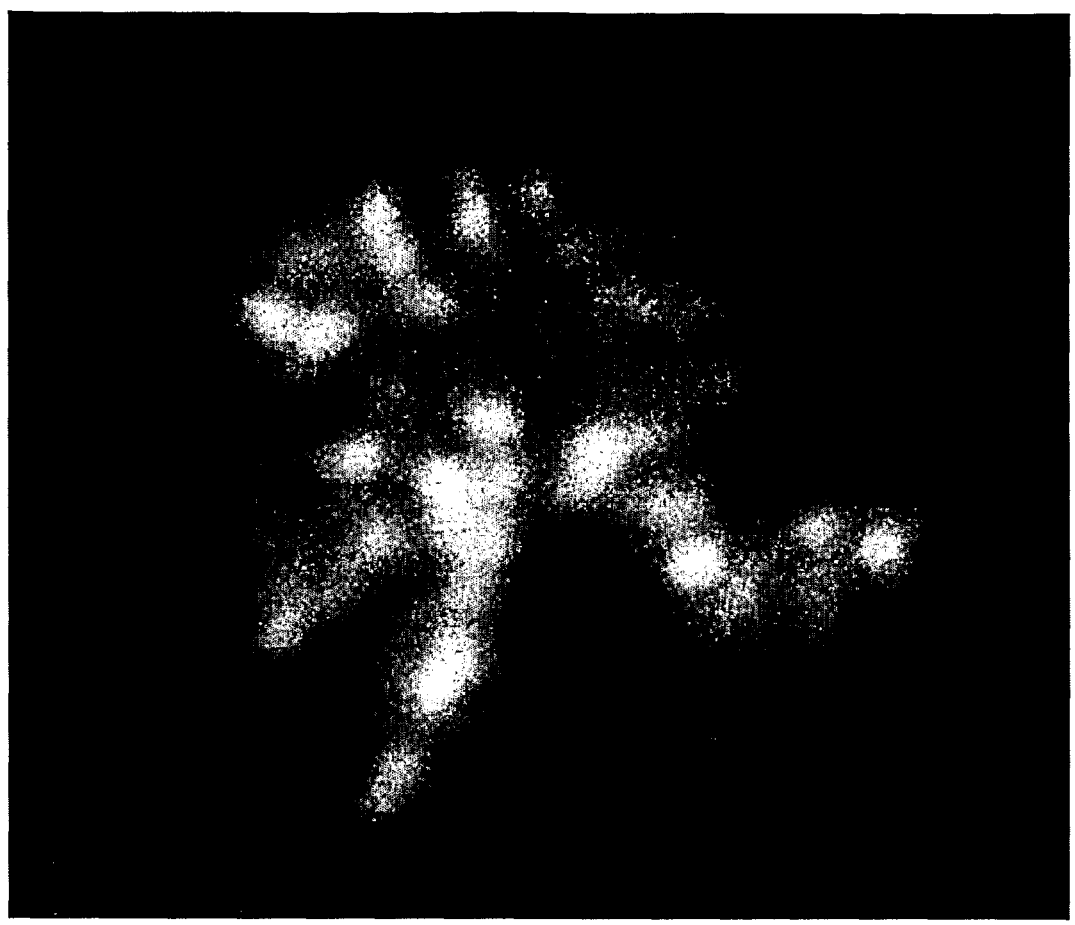
FIG. 11a: Gamma camera image of Tc-99m FibrinLite labelled microparticles of polystyrene sulphonate (Aminex 50W-X4; Bio-Rad) in an excised rabbit liver after regional arterial instillation under anaesthesia. The microparticles had average diameter 30 microns, so that they were carried by the arterial blood supply into the liver, where they lodged and were retained at limiting vessel sizes. Note the segmented distribution of label in the lobes of the excised liver, in contrast to the labelling seen in FIG. 10a above.

Imaging of Tc-99m FibrinLite Labelled Microspheres Following Instillation in the Arterial Vasculature of a Rabbit Liver Tc-99m FibrinLite (10 mCi) was pretreated for 30 min at 20° C. with 10 µg/mL protamine sulphate (Sigma P4505) in water (6.0 mL). The pretreated FibrinLite was added to prewashed polystyrene sulphonate microspheres (100 mg) of diameter 30 microns (Aminex 50W-X4; Bio-Rad) and binding allowed for 30 min at 20° C. with gentle mixing. The microspheres were rinsed 3 times with water (5.0 mL) before use. A New Zealand white rabbit was anaesthetised with isoflurane and the cystic and hepatic arteries exposed. A vinyl microcatheter was inserted in the cystic artery and successive small aliquots of microbead suspension bearing 3.0 mCi Tc-99m was slowly instilled so that the hepatic artery flow carried the microspheres into the liver. Gamma camera imaging of the rabbit confirmed that labelled microspheres had permeated the liver and the vast majority of label was retained there. Only a trace of labelled particles continued into the general circulation. After 60 min the rabbit was euthenased and the whole liver excised. Gamma camera imaging of the liver ex vivo (FIG. 11a) showed a distinctly segmented distribution of the label within the liver, in contrast to the complete perfusion of the liver seen with Tc-99m nanoparticles (see FIG. 10a above). Also, in contrast to the control experiment in Example 10, imaging of the body of the rabbit after removal of the liver showed no labelling of the spleen and bone marrow (FIG. 11b), so that retention of label on microspheres in the liver was virtually complete.

Figure 11B:
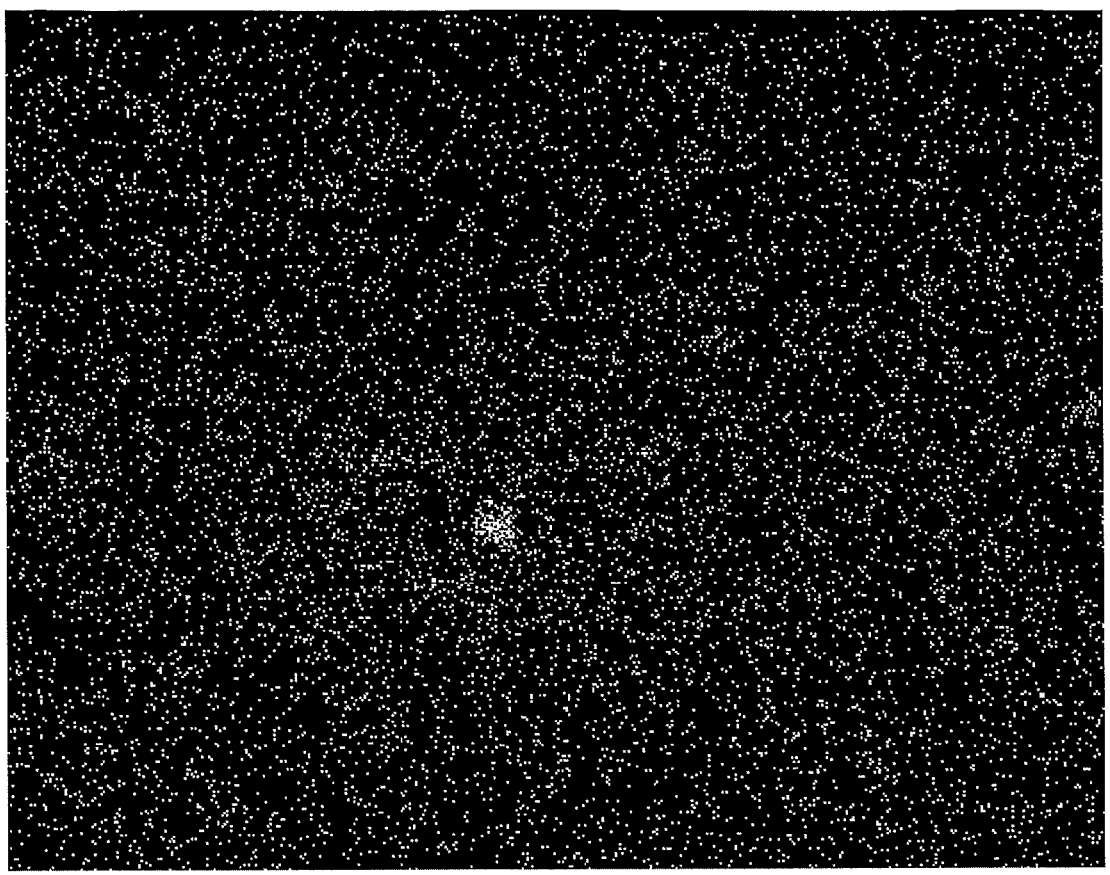
FIG. 11b: Gamma camera image of the body of the rabbit after removal of the liver shown in FIG. 11a above. In contrast to FIG. 10b above, labelling of spleen and bone marrow were absent. The small area of signal is due to remnant material from the liver after surgery.

These results showed that the labelling of the microspheres was stable under in vivo conditions in a rabbit. Gamma camera imaging of regionally instilled Tc-99m FibrinLite labelled microspheres showed efficient entrapment of label in the arterial vasculature of a rabbit liver (FIG. 11a), with insignificant leakage to the general circulation (FIG. 11b). This illustrates the potential use of the labelling method for medical imaging of synthetic polymers introduced into the body e.g for the purpose of regional therapy of cancer.

Example 12

Figure 12A:
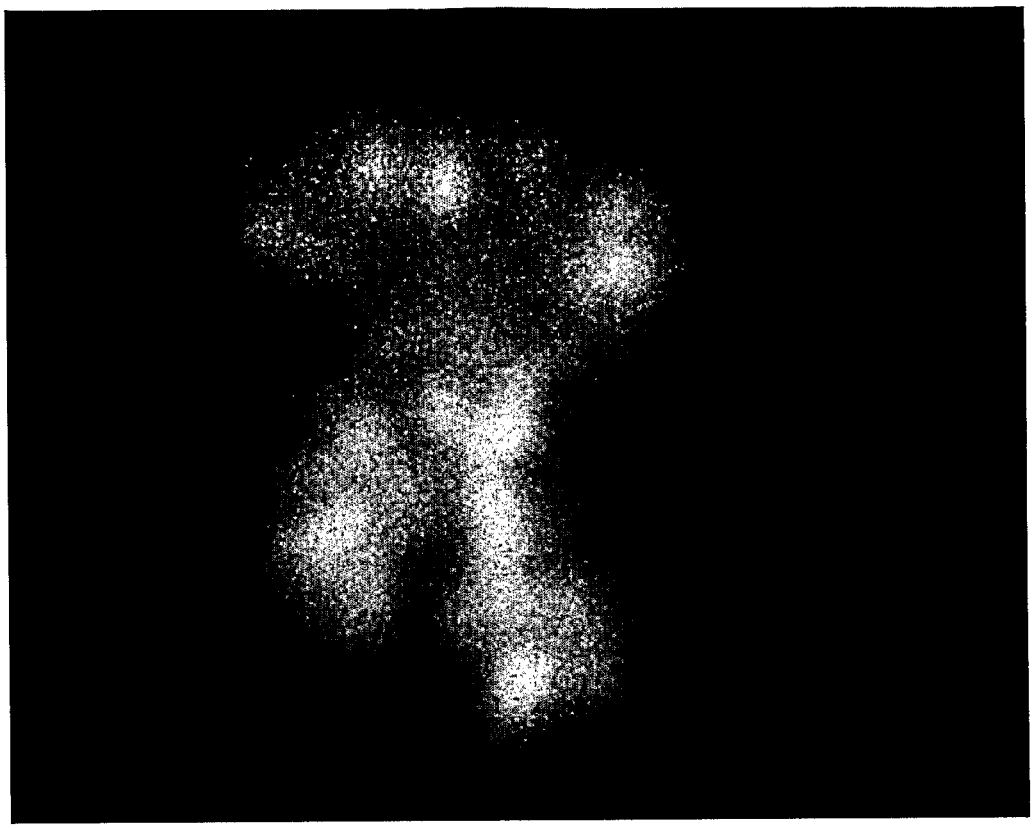
FIG. 12a: Gamma camera image of Tc-99m FibrinLite labelled SIR-Spheres microspheres in an excised rabbit liver after regional arterial instillation under anaesthesia. The SIR-Spheres microspheres were carried by the arterial blood supply into the liver, where they were retained at limiting vessel sizes. Note the segmented distribution of label in the lobes of the excised liver, in contrast to the labelling seen in FIG. 10a above.
Figure 12B:
FIG. 12b: Gamma camera image of the body of the rabbit after removal of the liver shown in FIG. 12a above. Note the weak imaging of the kidneys and bone marrow, in contrast to FIG. 10b.

Imaging of Tc-99m FibrinLite Labelled SIR-Spheres Microspheres Following Instillation in the Arterial Vasculature of a Rabbit Liver The SIR-Spheres microspheres used in this example had been aged over more than 100 half-life equivalents of the Y-90 therapeutic isotope ($t_{1/2}$=64 hours), so as to provide a "cold" Tc-99m SIR-Spheres microspheres sample for labelling with imaging isotope. Tc-99m FibrinLite (8.0 mCi) was pretreated for 30 min at 20° C. with 10 µg/mL protamine sulphate (Sigma P4505) in water (6.0 mL). The pretreated FibrinLite was added to prewashed SIR-Spheres microspheres (100 mg) and binding allowed for 30 min at 20° C. with gentle mixing. The SIR-Spheres microspheres were rinsed 3 times with water (5.0 mL) before use. A New Zealand white rabbit was anaesthetised with isoflurane and the cystic and hepatic arteries exposed. A vinyl microcatheter was inserted in the cystic artery and successive small aliquots of SIR-Spheres microspheres suspension bearing 3.5 mCi Tc-99m was slowly instilled so that the hepatic artery flow carried the microspheres into the liver. Gamma camera imaging of the rabbit confirmed that labelled SIR-Spheres microspheres had entered the liver and the vast majority of label was retained there. After 60 min the rabbit was euthenased and the whole liver excised. Gamma camera imaging of the liver ex vivo (FIG. 12a) showed a distinctly segmented distribution of the label within the liver, in contrast to the complete perfusion of the liver seen with Tc-99m FibrinLite nanoparticles (see FIG. 10a above). Also, in contrast to the control experiment with Tc-99m FibrinLite in Example 10 above, imaging of the body of the rabbit after removal of the liver showed that retention of label on SIR-Spheres microspheres in the liver was very efficient, so that only a trace of label was visible in the kidneys and bone marrow, and none was observed in the spleen (FIG. 12b).

These results showed that the labelling of SIR-Spheres microspheres was stable under in vivo conditions in a rabbit. Gamma camera imaging of regionally instilled Tc-99m FibrinLite labelled SIR-Spheres microspheres showed efficient entrapment of label in the arterial vasculature of a rabbit liver, with very minor leakage to the general circulation. This illustrates the potential use of the labelling method for medical imaging of synthetic polymers introduced into the body for the purpose of regional therapy of disease, e.g. cancer.

DISCUSSION

The examples herein demonstrate that high avidity labelling of synthetic polymers can be achieved through increased electrolyte concentration and or through pH conditions under which short range attractive forces predominate over long range electrostatic repulsive forces. The examples indicate that the binding between FibrinLite and polystyrene involves a hydrophobic interaction and since hydrophobic interactions are not disrupted, but actually strengthened by increased electrolyte concentrations, the binding can be utilized at physiological electrolyte concentrations. Using the methods described herein, FibrinLite nanoparticles are strongly retained on a polymer surface, and the radiolabel will not dissociate under electrolyte conditions that may be encountered in vivo.

The above examples illustrate the use of a simple electrolyte, sodium chloride, to induce binding of FibrinLite to a polymer surface. However polyions, especially polycations, were also found to strongly induce binding of FibrinLite to polymer surfaces, and at very low concentrations, e.g. polylysine at 0.5 micrograms/mL. It will be clear from the disclosure herein that surface treatment of FibrinLite with a polycation such as poly-lysine also enables the attachment of a wide range of organic substituents, e.g. polypeptides, antibodies, enzymes and cell-surface receptor ligands to the FibrinLite by standard methods of organic chemistry. This may be desirable for customising the FibrinLite for specific labeling and medical imaging applications in vivo, such as detection and localisation of marker proteins over-expressed on different types of human or animal tumours. Such use may provide an aid to diagnosis, prognosis, staging or postoperative monitoring of tumours, as well as detection of disease recurrence.

The above example illustrates the induction of binding of FibrinLite to polystyrene microwells. Closely similar findings were also obtained using polypropylene vials. Strong binding of FibrinLite to polypropylene was found after addition of simple electrolytes and especially after addition of polycations such as poly-lysine. Furthermore, the optimal concentrations for induction of binding were similar to those reported above for polystyrene. Polystyrene is an example of a polymer comprising chains of an aromatic subunit, styrene. Polypropylene is an example of a polymer comprising chains of an aliphatic subunit, propylene. Thus at the molecular level the chemistry of these two polymers is quite different, yet FibrinLite binding to both can be induced by the same concentration of electrolyte. In common is that the FibrinLite particles can make a close approach to the polymer surface where strong hydrophobic forces will predominate. A close approach is enabled by shielding the weak electrostatic repulsive forces with an appropriate concentration of an electrolyte. Binding is favoured by reducing the weak long range electrostatic repulsive forces, so that strong short range hydrophobic attractive forces can predominate.

The foregoing describes preferred forms of the present invention. It is to be understood that the present invention should not be restricted to the particular embodiment(s) shown above. Modifications and variations, obvious to those skilled in the art can be made thereto without departing from the scope of the present invention.

The invention claimed is:

1. A method of radiation therapy of a patient, the method comprising administering to an artery of said patient a medical device of a size range that, upon arterial administration, is capable of being entrapped in an arterial blood vessel network of a tissue and that comprises at least one microsphere, bead, capsule, microparticle, fibre, rod, filament, membrane, wafer, mesh, gauze, porous sponge, tube or stent, said medical device having incorporated therein or thereon a therapeutically effective amount of a radiolabeled synthetic polymer,
   wherein said radiolabeled synthetic polymer comprises a synthetic polymer complexed with a carbon encapsulated nanoparticle composite having a radioactive particulate core,
   wherein the carbon encapsulated nanoparticle composite is a carbon encapsulated $^{99m}$Tc, $^{113m}$In, $^{111}$In, $^{198}$Au, $^{64}$Cu, $^{213}$Bi, $^{57}$Co, $^{51}$Cr, $^{165}$Dy, $^{169}$Er, $^{59}$Fe, $^{153}$Gd, $^{166}$Ho, $^{177}$Lu, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Tl, $^{90}$Y or $^{169}$Yb nanoparticle having a diameter of 10 to 500 nanometers;
   wherein the synthetic polymer is polystyrene, polypropylene, polytetrafluorethylene (PTFE), expanded polytetraflourethylene (EPTFE), polyurethane, polyvinyl chloride, polyamides, polystyrene sulphonate, polyester, polyethylene terephthalate (PET), poly(butylene terephthalate) (PBT), poly(ethylene oxide) (PEO), polylactide (PLA), polyglycolide (PGA), poly(lactide-co-glycolide) (PLGA), poly(e-caprolactone), polydioxanone, trimethylene carbonate, polyanhydride, or poly[bis(p-carboxyphenoxyl)propane:sebacic acid; and
   wherein said radiolabeled synthetic polymer is prepared in an aqueous medium comprising (i) at least one of a polycation or an anionic surfactant; and (ii) an electrolyte concentration or a pH that is selected to promote in the aqueous medium short-range attractive forces between the carbon encapsulated nanoparticle and the synthetic polymer by attenuating long-range electrostatic repulsive forces so that the carbon encapsulated nanoparticle and the synthetic polymer comprise a complex that is stable under in vivo conditions in a mammal.

2. The method of claim 1, wherein the radiolabeled synthetic polymer is in the form of, or is incorporated into or onto, a bead, microparticle or microsphere.

3. The method of claim 1 which comprises treatment of cancer in the patient, wherein the radiation therapy is selective internal radiation therapy.

4. The method of claim 3, wherein the cancer is selected from (i) metastatic cancer present in the liver, originating from primary tumours of the colon, rectum, or breast, or (ii) primary liver cancer.

5. The method of claim 1, wherein the radioactive particulate core comprises a radioactive isotope or a radionuclide selected from the group consisting of $^{99m}$Tc, $^{198}$Au, $^{64}$Cu, $^{51}$Cr, $^{166}$Ho, $^{111}$In, $^{177}$Lu, $^{103}$Pd, $^{82}$Rb, $^{186}$Re, $^{153}$Sm, $^{89}$Sr, and $^{90}$Y.

6. The method of claim 1 wherein the synthetic polymer is selected from:
   polystyrene, polystyrene sulphonate, polypropylene, polytetrafluorethylene (PTFE), expanded polytetraflourethylene (EPTFE), polyester, polyethylene terephthalate (PET), poly(butylene terephthalate) (PBT), poly(ethylene oxide) (PEO), polylactide (PLA), polyglycolide (PGA), or poly(lactide-co-glycolide) (PLGA).

7. The method of claim 1 wherein the medical device comprises at least one microsphere, bead, or microparticle of a size range that, upon arterial administration, is capable of being entrapped in said arterial blood vessel network of a tissue.

* * * * *